United States Patent
Baklanov et al.

(10) Patent No.: US 6,662,631 B2
(45) Date of Patent: Dec. 16, 2003

(54) METHOD AND APPARATUS FOR CHARACTERIZATION OF POROUS FILMS

(75) Inventors: Mikhail Rodionovich Baklanov, Leuven (BE); Konstantin Petrovich Mogilnikov, Novosibirsk (RU); Karen Maex, Herent (BE); Denis Shamiryan, Leuven (BE); Fedor Nikolaevich Dultsev, Novosibirsk (RU)

(73) Assignees: Interuniversitair Microelektronica Centrum, Leuven (BE); Technokom-Centre Advanced Technology, Novosibirsk (RU); XPEQT, Bevgivj (CH)

( * ) Notice: Subject to any disclaimer, the term of this patent is extended or adjusted under 35 U.S.C. 154(b) by 0 days.

(21) Appl. No.: 10/194,137

(22) Filed: Jul. 12, 2002

(65) Prior Publication Data

US 2003/0094032 A1 May 22, 2003

Related U.S. Application Data

(60) Continuation-in-part of application No. 09/931,419, filed on Aug. 16, 2002, now Pat. No. 6,435,008, which is a division of application No. 09/529,390, filed on Jun. 19, 2000, now Pat. No. 6,319,736.
(60) Provisional application No. 60/098,247, filed on Aug. 28, 1998, and provisional application No. 60/383,004, filed on May 24, 2002.

(51) Int. Cl.[7] .................. H01L 21/66; G01N 15/08; G01N 21/21; G01L 01/24; G01M 09/00

(52) U.S. Cl. ............... 73/38; 73/800; 73/866; 73/789; 702/43; 702/82

(58) Field of Search ............... 73/38, 37, 866, 73/800, 789, 78; 438/16; 702/43, 82

(56) References Cited

U.S. PATENT DOCUMENTS

| | | | | | |
|---|---|---|---|---|---|
| 4,541,059 | A | * | 9/1985 | Toshihiko | 364/508 |
| 4,719,583 | A | * | 1/1988 | Takafuji et al. | 364/506 |
| 5,297,062 | A | * | 3/1994 | Cresson et al. | 364/564 |
| 5,372,958 | A | * | 12/1994 | Miyasaka et al. | 437/40 |
| 5,433,215 | A | * | 7/1995 | Athanasiou et al. | 128/774 |
| 5,668,305 | A | * | 9/1997 | Chi et al. | 73/37 |
| 5,767,399 | A | * | 6/1998 | Smith et al. | 73/152.11 |
| 5,777,245 | A | * | 7/1998 | Chandrachood et al. | 73/865.9 |
| 5,907,093 | A | * | 5/1999 | Lehmann | 73/49.3 |
| 5,979,244 | A | * | 11/1999 | Michaelis | 73/800 |
| 6,016,703 | A | * | 1/2000 | Blyler, Jr. et al. | 73/705 |
| 6,055,053 | A | * | 4/2000 | Lesniak | 356/366 |
| 6,082,184 | A | * | 7/2000 | Lehmann | 73/49.3 |
| 6,219,139 | B1 | * | 4/2001 | Lesniak | 356/366 |
| 6,431,007 | B1 | * | 8/2002 | Roy | 73/800 |
| 6,435,010 | B1 | * | 8/2002 | Johnson et al. | 73/40 |
| 6,499,355 | B1 | * | 12/2002 | Potyrailo | 73/762 |

* cited by examiner

Primary Examiner—Hezron Williams
Assistant Examiner—David Wiggins
(74) Attorney, Agent, or Firm—McDonnell Boehnen Hulbert & Barghoff

(57) ABSTRACT

A method and apparatus for evaluation of films, such as low-k thin films with nano-scale pores, are provided. The evaluation may include characterization of the pore structure, the characterization results in determining pore sizes, hence obtaining pore size data. Moreover, the characterization may result in a non-destructive evaluation of mechanical properties, in particular the Young's Modulus, or the effect of interfering physical & chemical factors such as Pore Killers. Further, in line monitoring or studying of pore structure porosity and pore size distribution (PSD) of low-k films and evaluation of the mechanical properties of porous low-k films simultaneously using the same set of experimental data is provided.

10 Claims, 14 Drawing Sheets

METHOD AND APPARATUS FOR CHARACTERIZATION OF POROUS FILMS

REFERENCE TO RELATED APPLICATIONS

The current patent application claims priority to U.S. patent application Ser. No. 60/383,004 filed on May 24, 2002. The current patent application is a continuation-in-part application of U.S. patent application Ser. No. 09/931,419, now U.S. Pat. No. 6,435,008, which was filed on Aug. 16, 2001. U.S. patent application Ser. No. 09/931,419, now U.S. Pat. No. 6,435,008 is a divisional of U.S. patent application Ser. No. 09/529,390, now U.S. Pat. No. 6,319,736. U.S. patent application Ser. No. 09/529,390, now U.S. Pat. No. 6,319,736. U.S. patent application Ser. No. 09/529,390, now U.S. Pat. No. 6,319,736 claims priority to U.S. patent application Ser. No. 60/098,247. This application incorporates by reference U.S. patent application Ser. No. 60/383,004 in its entirety. This application incorporates by reference U.S. Pat. No. 6,435,008 in its entirety. This application also incorporates by reference U.S. Pat. No. 6,319,736 in its entirety. This application further incorporates by reference U.S. patent application Ser. No. 60/098,247 in its entirety.

BACKGROUND OF THE INVENTION

As integrated circuit feature sizes continue to shrink, new low dielectric constant (low-k) materials are needed to address problems with power consumption, signal propagation delays, and cross talk between interconnects. One avenue to low-k dielectric films is introduction of nanometer scale pores to lower its effective dielectric constant. However, the pore structure strongly affects important material properties such as mechanical strength, moisture uptake, thermal expansion, and adhesion to different substrates. Therefore, characterization of the pore structure, in particular the pore size distribution and mechanical properties, is strongly needed to optimize and develop new low-k materials and processes.

Traditional methods used for the porosity characterization in bulk materials are hardly applicable to thin films because the total pore volume and surface area are too small. For this reason, advanced non-destructive methods, such as small-angle neutron and X-ray scattering (SANS and SAXS) combined with specular X-ray reflectivity (XRR) and positron annihilation spectroscopy (PALS, PAS) have recently been developed to characterize the pore size and porosity of thin porous films. Although these new techniques are based on different physico-chemical principles, few systematic studies reported so far show that the results of the measurements are in reasonable agreement.

Low stiffness properties of porous low-K films is one of key factors limiting their introduction into ULSI technology. A compromise must be reached between low dielectric constant and sufficient mechanical strength for the material to survive technological steps. There is also lack of useful and accessible techniques, which can accurately provide absolute values of the mechanical characteristics.

In PALS and PAS, films are irradiated with a focused beam of several keV positrons. Positrons form positronium (Ps)—the electron-positron bound state—that is trapped in the pores where their natural lifetime of 142 ns is reduced by annihilation during collisions with the pore walls. The reduced lifetime $\tau(Ps)$ can be correlated with pore size. Ps lifetime histograms are recorded, and the lifetime distribution curves are obtained with a fitting program specified for this purpose. The distribution curves are transformed into pore size data, using pore geometries. The film porosity can be calculated by comparison of measured photon annihilation ratio of Ps atoms. In PALS, the porosity characterization needs deposition of a special barrier to compare the Ps intensity in free and capped films. PAS and PALS are efficient for the evaluation of bi-modal pores (like MSSQ). If pores are bi-modal, they give information related to their size and relative concentration. PALS and PAS are useful for characterization of pore interconnectivity and can be used for evaluation of diffusion barriers by detecting of Ps escaping from the film trough the voids in the barrier. However, because $\tau(Ps)$ also depends on the wall nature, sometimes it is difficult to obtain the pore size from $\tau(Ps)$: for instance, in the case of organic polymers. If all pores are open, one needs to apply a capping layer: otherwise Ps escape to vacuum and give the natural $\tau=142$ ns.

In SANS, the absolute scattered neutron intensity, I, plotted against the scattering vector $q=(4\pi/\lambda)\sin(\theta/2)$ where $\theta$ is the scattering angle from the incident beam path and $\lambda$ is the neutron wavelength (6 Å). The SANS intensity plotted versus q is a function of the porosity and wall density. The functional form is determined assuming a random two-phase (void+solid) structure. The film thickness and overall electron density are evaluated by the XRR measurements and are combined with the film composition data obtained by RBS and FRES so that the overall film density is determined. Since the film density is also a function of the porosity and skeleton density, these values are obtained by solving for the unknowns in the equations from SANS and XRR.

Recently, a simple X-ray scattering method for thin film evaluation was reported. The pore size is calculated by comparing the observed profile of scattering intensity and results of simulation. This approach is convenient to get general information without details because only effective pore size is calculated. If the film has bi-modal pores, the effective pore size depends on the ratio between small and large pores. For instance, if they have the same volume, the SAXS pore size is closer to the small pores due to the larger number of interfaces. The film porosity is calculated by normalization of the XRR film density to the skeleton density. This necessitates the assumption that the skeleton is identical to the dense, non-porous prototype. Sometimes such an assumption is not justified. The non-porous prototype may also be not available (for instance, in the case of CVD SiOCH films). This method is not efficient for evaluation of the pores interconnectivity, for evaluation of diffusion barriers and, generally, SAXS is not able to distinguish between pores and particles.

Nanoindentation (NI) is the most common method for obtaining stiffness of thin films. However, NI overestimates stiffness because of several possible reasons: (a) Stiffening by the substrate. For such thin films the NI tip may always feel the effect of the substrate and thus overestimate Young's Modulus (E); (b) Viscoelasticity. Polymers are known to show large viscoelastic effects which are likely to cause higher E values to be obtained; (c) Tip-film interactions. Effects such as densification or pile-up under the tip have not been quantified. The interactions of a tip with such a porous matrix are not well understood. Additionally, NI is destructive and therefore it is not applicable for in-line monitoring of low-k films.

Two different non-destructive methods have recently been successfully used for evaluation of stiffness properties of porous low-K films. Results of the stiffness measurements of MSSQ based porous low-K films by Surface Acoustic Wave Spectroscopy (SAWS) and Brillouin Light Scattering (BLS)

are in good agreement one with another but E values calculated for various low-K films are ≈3 times lower than NI. The film density and porosity calculated from the same SAWS data correlate excellently with Specular X-Ray Reflectivity. These facts suggest that the E values obtained by SAWS and BLS are real and accurate.

In the SAWS method for non-destructive characterization of density and Young's Modulus of low-k films, surface acoustic wavepackets are generated thermoelastically from absorption of laser pulse energy at the layer/substrate interface. The laser pulse energy (337 nm wavelength) is focused into a thin line on the sample, and causes rapid expansion of the locally heated source, giving rise to stresses and generating surface acoustic wavepackets propagating along the sample. The wideband SAW wavepackets are detected by a piezoelectric foil with a steel-wedge transducer at different relative propagation distances (here 15 mm) on the sample. The broadband SAW wavepacket (approx. 20–100 MHz frequency range) propagates in both layer and substrate and becomes dispersed because waves of different frequency sample a different proportion of layer and substrate, with different net elastic properties, and the wave velocity is therefore frequency dependent. From a Fourier transform technique one extracts the frequency-dependent velocity dispersion curve. Assuming that thickness and Poisson's ratio are known, the density and Young's modulus of the layer are obtained from the best-fit parameters of the theoretical to the measured dispersion curve. The SAWS film density is in good agreement with XRR. Although SAWS is not able to measure the pore size, a unique feature of this method is the possibility of non-destructive evaluation of mechanical properties (Young's Modulus).

SUMMARY OF THE INVENTION

It is the aim of the invention to provide a method and apparatus for evaluation of films, more especially low-k thin films with nano-scale pores.

In a first aspect thereof, said evaluation may include characterization of the pore structure, said characterization results in determining pore sizes, hence obtaining pore size data.

In a second aspect thereof, said characterization may result in non-destructive evaluation of mechanical properties, in particular the Young's Modulus.

In a third aspect of the invention, a method is provided which is suitable for both in line monitoring or studying of pore structure porosity and pore size distribution (PSD) of low-k films and evaluation of the mechanical properties of porous low-k films simultaneously using the same set of experimental data.

Said method and apparatus for characterization can provide information useful for the development of new types of low-k dielectrics and optimisation of a variety of technological processes, for instance in the phase of their integration but also in quality control testing and process control.

Said method and apparatus is based on ellipsometric porosimetry, (also called EP), which evaluates optical characteristics of a porous film during the vapor adsorption in the pores. The proposed characterization does not need complicated calculations and therefore does not need complex arithmetical processors nor large memories. Said method and apparatus uses data obtained by ellipsometric porosimetry.

In a first aspect of the invention, a method for characterizing the pore structure of a film from ellipsometric measurements is disclosed. Said method determines a computed pore size distribution, meaning at least the amount of pores of at least two different sizes, of the pores of a film or just a rough approximation thereof from said ellipsometric porosimetry measurements.

In a first embodiment thereof, a first determination on the quality of said film, in terms of presence of pore-killers, is made based on said computed pore size distribution. In a further embodiment thereof said first determination is used for either making the film sample under investigation a candidate for rejecting in a quality control setting or suggesting possible required adaptations of the film production process parameters are determined in an on-line process control environment. In a second embodiment said first determination is verified by using the same ellipsometric porosimetry measurements, more in particular the thickness of said film. In case it is clear that no film swelling is present, said first determination is confirmed. Then film being candidate for rejection are finally rejected or the need for process parameter changes is confirmed.

Porous films may be prepared by several methods including Spin-on-glass technology and CVD.

The invented method comprises the steps of performing ellipsometric measurements on a film with pores with various pore sizes and computing from said measurements at least an approximation or an indication of the pore size distribution. Said ellipsometric measurements result in data of the refractive index (first data set) and the thickness (second data set) of said film as function of the pressure within the pressurized chamber wherein said film is placed for measuring. Said computation can exploit steps of determining a first slope of the curve defined by parts of the first data set and a second slope by parts of the second data set. The indication of the possible presence of pore-killers relies on said first slope, for instance when said first slope exceeds a first threshold value. Confirmation of said presence is performed when said second slope is below a second threshold value.

In an embodiment of this invention, a method as recited in the previous embodiments is disclosed wherein said film is a porous film used as insulating layer in semiconductor processing.

In an embodiment of this invention, a method as recited in the previous embodiments is disclosed wherein said ellipsometry measurements are performed according to patent application WO 00/1299 and U.S. Pat. No. 6,319,736.

In an embodiment of this invention, a method as recited in the previous embodiments is disclosed wherein said method is for quality testing said film. In an embodiment of this invention, a method as recited in the previous embodiments is disclosed further comprising the steps of accepting or rejecting the film.

In an embodiment of this invention, a method as recited in the previous embodiments is disclosed further comprising the step of changing the parameters of the film fabricating process in response to any determination of pore size or a mechanical property according to the present invention. In an embodiment of this invention, a method as recited in the previous embodiments is disclosed wherein said method is used in a process control unit, said process control unit being for controlling the fabrication process of porous layers.

In a second aspect of the invention, a method for determining the Young's modulus of a film, placed in a pressurized chamber, comprising the steps of determining via ellipsometric measurements a set of data relating to the change of thickness of the film versus said pressure in said chamber; and calculating the Young's modulus of said film from said set of data. Alternatively formulated this aspect of the invention is a method for determining the Young's modulus of an element which is positioned in a pressurizable chamber, filled with a gaseous substance, said method comprising the steps of performing ellipsometric measurements on said element at a pressures being less than equilibrium vapor pressure of said gaseous substance, to determine data on the film thickness as function of said pressure; and determining the Young's modulus from said data.

In an embodiment of the invention a method as recited in the second aspect of the invention is described wherein said film is a porous film. In a further embodiment of this second aspect of the invention, a method as recited in any of the embodiments is disclosed wherein said film is a porous film used as insulating layer in semiconductor processing.

In an embodiment of this second aspect of the invention, a method as recited in any of the previous embodiments is disclosed wherein said first step is performed according to patent application WO 00/1299 and granted U.S. Pat. No. 6,319,736, which are incorporated herein by reference in their entirety.

In an embodiment of this second aspect of the invention, a method as recited in any of the previous embodiments is disclosed wherein said method is used for quality testing said film. In a further embodiment thereof said quality testing method comprises the steps of accepting or rejecting the film, e.g. in accordance with a threshold value.

In an embodiment of this second aspect of the invention, a method as recited in any of the previous embodiments is disclosed wherein said method is used as part of an on-line process control method for controlling the fabrication process of said film. In a further embodiment thereof said process control method comprising the steps of changing the parameters of the film fabricating process. Fabrication process parameters of the spin-on-glass technology which are changeable via the process control unit are, for example, spinning rotation speed, the length of the heating substeps and their respective heating temperature. Fabrication process parameters of the CVD film making process which are changeable by the process control unit are, for example, the length and temperature of the annealing step.

Alternatively the invention is available as program storage devices readable by a machine and encoding a program of instructions for executing the above described methods. Instruction may be provided for loading data, obtained by performing at least one ellipsometric measurement, computing steps on said data and outputting computed information of said film.

DETAILED DESCRIPTION OF THE PRESENTLY PREFERRED EMBODIMENT(S)

Figure 1:
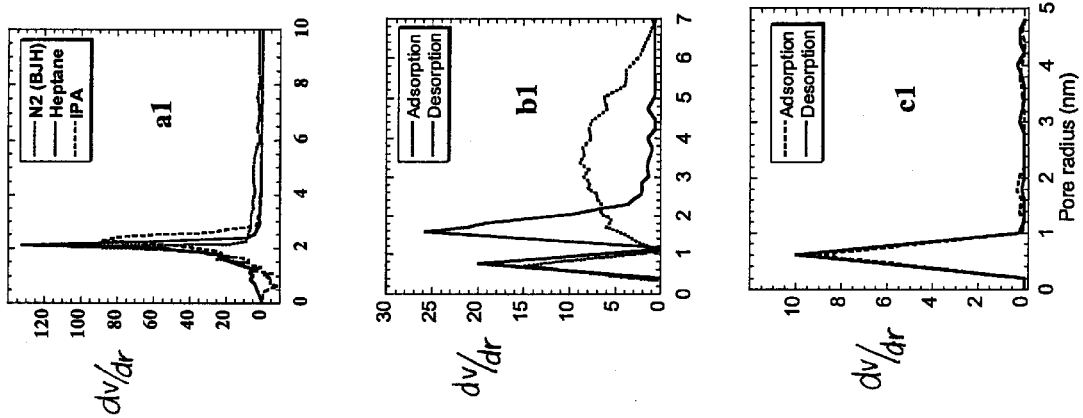
FIG. 1 are graphs showing adsorption/desorption isotherms, open porosity and pore size distribution in different types of low-K dielectrics: mesoporous XLK film (designated as "a", "a1"), MHSSQ film with bi-modal porosity (designated as "b", "b1") and microporous SiOCH (designated as "c", "c1").
Figure 1:
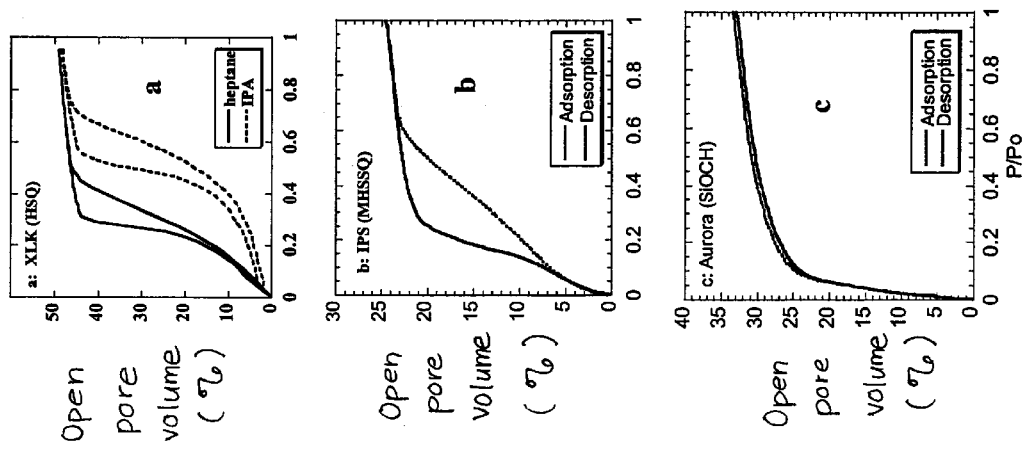

Determination of the Presence of Pore Killers

Analysis of the measurements obtained by ellipsometry, more in particular the refractive index as function of the relative pressure, can indicate, by evaluating the slope, the presence of pore-killers, meaning the presence of a substantial amount of pores with a large size. Evaluating the fitness of a film requires reliable determination of the pore size distribution. As the refractive index as function of relative pressure can also change for high relative pressure due to film swelling rather than due to the presence of large pores, this effect must be recognized, preferably without having to perform additional cumbersome measurements. As ellipsometry also provides information on the thickness of the film as function of relative pressure, this extra measurement is used for indicating the presence of film swelling. Hence from ellipsometry measurements one can determine besides the overall porosity of the film, a computed pore size distribution. From said computed pore size distribution one can decide whether said film is a candidate for rejection, due to the presence of large pores. From the ellipsometry thickness measurements, one can justify that the computed pore size distribution indeed indicates the pore size distribution in the film or not, if the film is swelling. Both the swelling case and the non-swelling case with pore-killers will usually result in final rejection of the film. The combined thickness and refractive index evaluation can use threshold evaluation of slopes, in predetermined pressure ranges.

Hence by performing ellipsometric measurements on a film a first data set of the refractive index of the film as function of the pressure and a second set of data of thickness of the film versus the pressure is obtained. From said data sets first and second slopes are determined respectively. The presence of pore-killers is indicated if said first slope exceeds a first threshold value and if said second slope is below a second threshold value. In an embodiment of this invention said slope determinations are performed for pressure values exceeding third threshold value.

The following paragraph describes a film which is a porous low-k film. This is only illustrative and the present invention may be used for all types of film of which the characteristics should be determined. The porosity measurement is based on the methods and apparatus described in patent application WO 00/1299 and issued U.S. Pat. No. 6,319,736, which are incorporated herein by reference.

The relation between the optical characteristics and the pore volume V of the porous film is described by the Lorentz-Lorenz equation:

$$B_p = \Sigma N_i \alpha_i = \frac{3}{4\pi}\left[V \cdot \frac{(n_1^2-1)}{(n_1^2+2)} + (1-V) \cdot \frac{(n_s^2-1)}{(n_s^2+2)}\right] \quad (1)$$

where $B_p=(n_p^2-1)/(n_p^2+2)$ is the effective polarizability of a unit of volume of the porous film, $N_i$ and $\alpha_i$ are the number of molecules and the molecular polarizability of the material components. $n_p$ is the measured refractive index of $$V = 1 - \frac{B_p}{B_s} = 1 - \left[\frac{(n_p^2-1)}{(n_p^2+2)}\right] / \left[\frac{(n_s^2-1)}{(n_s^2+2)}\right] \quad (2)$$

the porous film, $n_s$ and $n_1$ are the refractive index of the film skeleton and of the material inside the pores, respectively. V is the relative pore volume (porosity). These equations are also valid if a liquid with a known refractive index $n_{liq}$ fills the pores ($n_1=n_{liq}$). The adsorbate amount inside the pores is calculated using the refractive index and density of the liquid adsorbate. Ellipsometry allows measurement of both the refractive index and the film thickness d, therefore the adsorbate volume, that is equal to the open pore volume, can be calculated. The relative volume of open and closed pores is calculated by comparison of the results obtained before and after adsorption. This analysis gives information related to the pores interconnectivity. If the porous film is anisotropic, the depth profile can be analyzed using a multilayer optical model. Two different theories can be used for the PSD (Pore Size Distribution) calculation in mesoporous and microporous films. The PSD calculation in the mesoporous films uses the phenomenon of progressive emptying of a porous system initially filled at $P=P_o$. The calculation is based on analysis of hysteresis loop appearing during the adsorption and desorption because the effective radius of curvature of condensed liquid meniscus is different during the adsorption and desorption. The adsorptive vapor condenses in the pores at the vapor pressure (P) lower than the equilibrium pressure of a flat liquid surface ($P_o$). Dependence of the relative pressure ($P/P_o$) on the meniscus curvature is described by the Kelvin equation:

$$\ln\left(\frac{P}{P_0}\right) = -\frac{f \cdot \gamma \cdot V_L \cos\theta}{r_K \cdot RT} \quad (3)$$

where $\gamma$ and $V_L$ are surface tension and molar volume of the liquid adsorptive, respectively. $\theta$ is the wetting angle of the adsorptive, f=1 for slit-shaped pores and f=2 for cylindrical pores. If the radius of a cylindrical pore is $r_p$, then $r_p=r_K+t$ and t is the thickness of the layer adsorbed on the pore walls. Values of t are obtained from the adsorption of the same adsorptive on a non-porous sample and are defined by the BET equation. Initial experimental data for the calculations are the ellipsometric angles Δ and Ψ. EP software allows calculating the change of n and d during the adsorption and desorption, pores volume, PSD and specific surface area. The specific surface area of each small group of pores $\delta A_i$ are calculated from the pore volume and pore radius as $\delta A_i=\delta V_i/r_i$. By summing the values of $\delta A_i$ over the whole pore system, a value of the cumulative surface area is obtained. In micropores with widths of order of a few molecular diameters, the Kelvin equation no longer remains valid. Not only would the values of the surface tension and the molar volume deviate from those of the bulk liquid adsorptive, but also the concept of a meniscus would eventually become meaningless. To analyze the microporous films, a method based on a theory developed by Dubinin and Radushkevitch (DR) can be used. The DR uses change of adsorption potential when the pore diameter is comparable with the size of the adsorptive molecules. The process involved is the micropore volume filling rather than layer-by-layer adsorption on the pore walls. Adsorption potential A and characteristic adsorption energy $E_o$ are function of the micropore size and amount of adsorption W at the relative pressure $P/P_0$:

$$W = W_0 exp[-(A/E)^n]$$

$$(n=2; E=\beta E_0; A=RT\ln(P_0/P)) \quad (4)$$

Here, $W_0$ is the micropore volume, $\beta$ is the affinity coefficient. The linear plot of $\ln W$ versus $A^2$ leads to $W_0$ and $\beta E_0$. The $\beta E_0$ value provides the isosteric heat of adsorption. $E_0$ gives the average pore width $w_o=K/E_0$ where $K\approx12$ is a coefficient slightly changing with $E_0$. The DR analysis can provide the essentially important parameters on the micropore structure such as the micropore volume, the average pore size and the isosteric heat of adsorption. The EP software recognizes presence of micropores in the film during the analysis of adsorption and desorption isotherms and calculates both the mesopore and micropore characteristics. Traditional $N_2$ adsorption porosimetry (BJH) is based on measurement of mass or volume of adsorbate condensed in the pores. Therefore, this method gives information only related to open pores. If material is swelling during the adsorption, the measured adsorptive volume corresponds to the swelled film and is larger than the real concentration of open pores. EP is able to detect change of the film properties during the adsorption. Therefore, additional information related to the film swelling during the adsorption can be obtained. EP allows compare open and full porosity and to make conclusion about the pore interconnectivity.

In the following selected experimental results obtained using an EP tool equipped with in situ spectroellipsometer (SE) are presented.

FIG. 1 shows typical adsorption/desorption isotherms and PSD for the low-k films that have been developed for the ULSI (Very Large Scale Integration) technology. Hydrogen and methyl-silsesquioxane (HSSQ and MSSQ) based porous spin-on-glass (SOG) films, formed on Si wafers and a CVD SiOCH film are shown. The HSSQ based XLK film (FIG. 1(a)) is a typical mesoporous film. Adsorption/desorption isotherm has a well-pronounced hysteresis loop. The saturation points for the different adsorptives are very close one to another and correspond to open porosity equal to 48%. Comparison of this value with the full film porosity measured by SE allowed us to conclude that all pores in this film are interconnected. This graph also demonstrates that the choice of an appropriate adsorptive can shift the isotherm to the different P/Po range because of different molecular characteristics. Such kind of experiments helps to approve the validity of the Kelvin equation and known as the Gurvitch test. According to the Gurvitch rule, if the adsorptives with different molecular characteristics give the same pore size, the Kelvin equation is still valid. A perfect agreement of PSD calculated from the adsorption of different adsorptives is obtained. PSD calculated from the EP data is also in good agreement with PSD obtained by standard $N_2$ adsorption (BJH) porosimetry from the same set of low-k film (FIG. 1(a1)). FIG. 1b shows the adsorption/desorption isotherm and PSD obtained for a MHSSQ based low-k film (IPS). This film shows a bi-modal porosity (both meso- and micropores are present in the film). The micropores are probably an intrinsic property of the MSSQ based materials and related to the replacement of hydrogen by the methyl group with a larger size (if comparing with HSSQ). The micropores are responsible for the additional slope in the adsorption/desorption isotherm at low-pressure region ($P/P_o<0.1$). FIG. 1(b1) shows PSD in this film. FIG. 1(c) shows EP results for CVD SiOCH film. The SiOCH films are becoming popular because they have chemical properties more close to the traditional $SiO_2$ films than organic polymers developed for the same generation of low-k dielectrics (k=2.5–2.8). Therefore most technological processes developed for $SiO_2$ can be used without a significant change. Their porosity is lower than that of the above-mentioned SOG films. The SiOCH films are microporous and the DR method can be used for the calculations (FIG. 1(c1)).

There are several examples of methods for preparation of porous films. A first method is called Spin-on-glass technology. In a first step, a $SiO_2$ Gel is prepared, said Gel containing porogen (macromolecules with size close to future pores). After spinning on top of your wafer (thickness can be varied by changing of rotation speed of the substrate), the wafer is heated. In the first substep of this heating (normally, temperature is between 200–300° C.), a film backbone (skeleton) is formed but porogen is still inside of the film. In the second substep of this heating (for example, 350–400° C.) curing is performed. During the curing, porogen macromolecule is destructed and small molecules leave film by diffusion through the film. Finally, all these procedures have to leave pores inside the film with size close to size of porogen macromolecules.

A second method for preparation of porous films is CVD. Organic-onorganic hybride can be used to form carbon doped $SiO_2$. For instance, a typical precursor is methyl silanes: $SiH_4+O_2$ gives $SiO_2$, but for preparation of carbon doped $SiO_2$ one uses $SiH(CH_3)$3-trimethylsilane, . . . , SiH3(CH3)—methylsilane. As a result, one has a film that still contains some Si—$CH_3$ bonds. This bonds thermally less stable than SiH, therefore, during the annealing some of them can leave film and form free volume (micropores).

Figure 2:
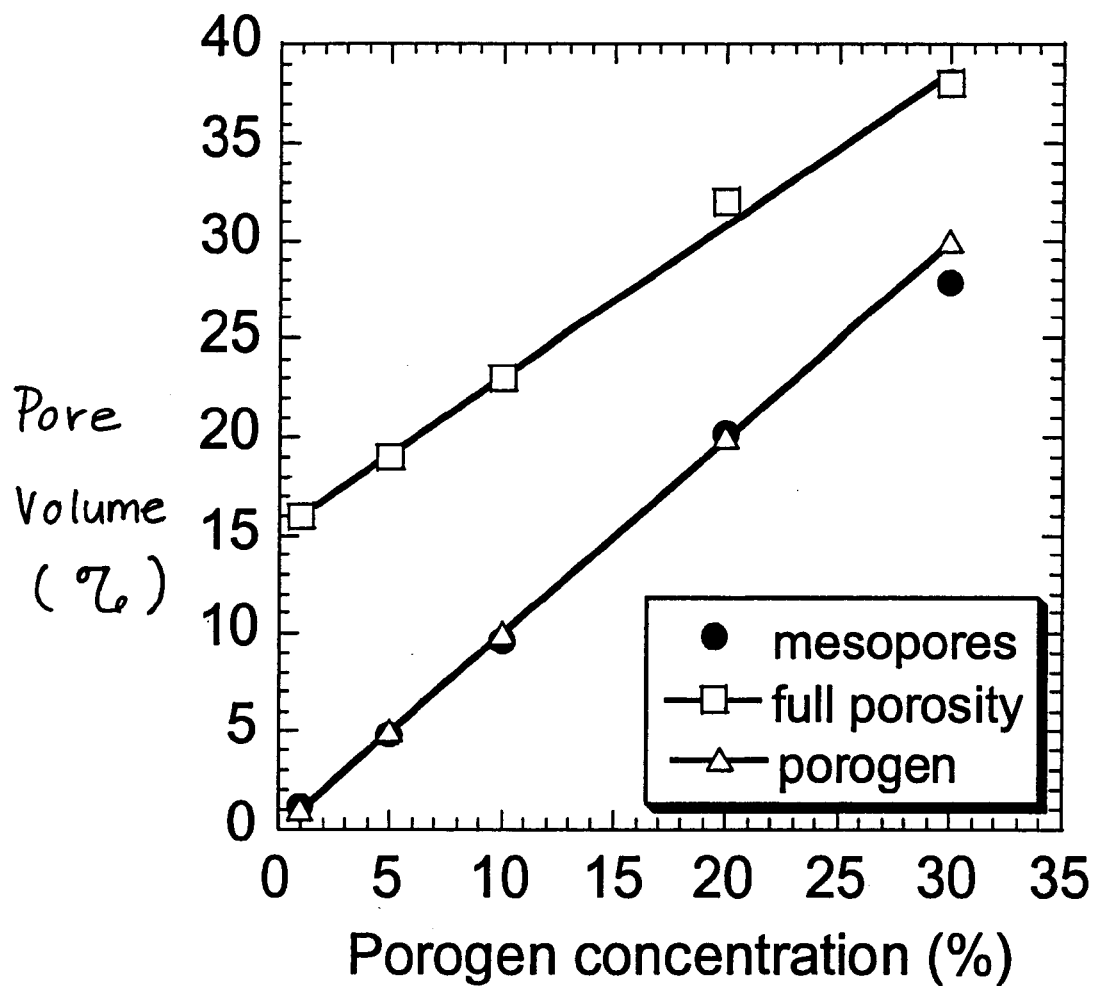
FIG. 2 is a graph showing pore volume versus the porogen concentration (MSSQ based low-K film). Straight line with the triangle symbols corresponds to the pore volume equal to the porogen concentration.
Figure 3:
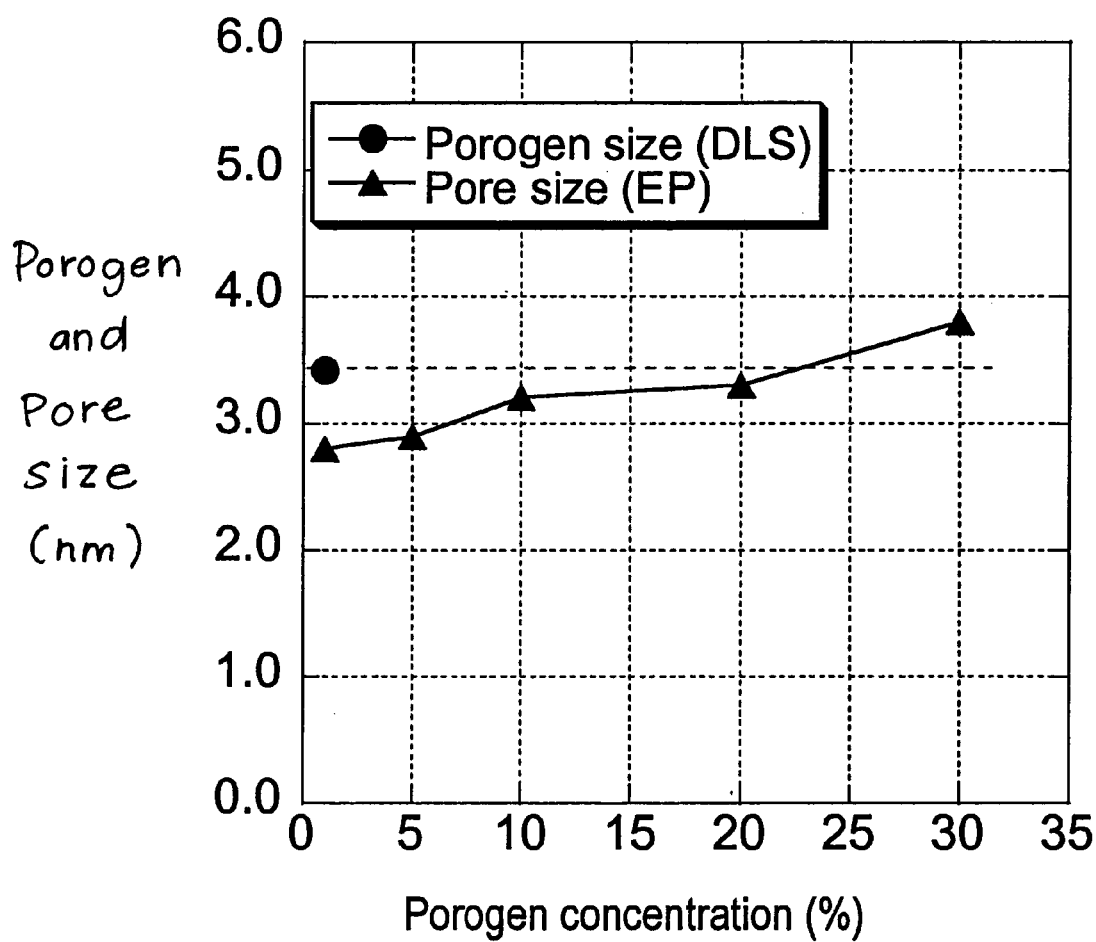
FIG. 3 is a graph of porogen and pore size versus the porogen concentration (MSSQ based low-K film). The mesopores size correlates well with the porogen size.

Another suitable method to prepare a porous film with controllable pore size is the templated vitrification of low molecular weight oligomers by macromolecular porogens. The porogen macromolecule defines the pore size. No dependence of the pore size on porosity and a good correlation between the mesopore volume and the porogen concentration were demonstrated for a MSSQ based film. EP showed a bi-modal porosity in these films. Micropores with radii 0.7–0.8 nm are an intrinsic property of MSSQ that define the relatively low dielectric constant of dense films. PALS also detected the micropores in the MSSQ based films. The film prepared with 1% of porogen already contained ≈14–16 volume percents of micropores. The mesopore volume correlates well with the porogen concentration (FIG. 2) and the pore size correlates with size of the porogen molecule (FIG. 3). The skeleton density of the films calculated by combination of EP and SAWS data is close to 1.4 $g/cm^3$ that is typical for the dense MSSQ films. This fact is in agreement with EP data showing that the skeleton refractive index is close to the refractive index of dense MSSQ (n=1.44–1.45). An insignificant increase of the skeleton density with increasing porosity is related to the stress related shrinkage of the skeleton. For the same reason, the mesopore size slightly increases with porosity.

Diffusion barriers on top of low-k dielectrics are needed because of significant Cu mobility in dielectric materials. This problem becomes even more important for the porous low-k dielectrics. A number of papers have been dedicated to the study of the barrier performance on top of the porous films. Increasing the barrier thickness allows capping all pores but the barrier should be thin enough to provide the low effective resistance of the metallization stack. Therefore, non-destructive determination of the minimal barrier thickness is an important issue.

Figure 4:
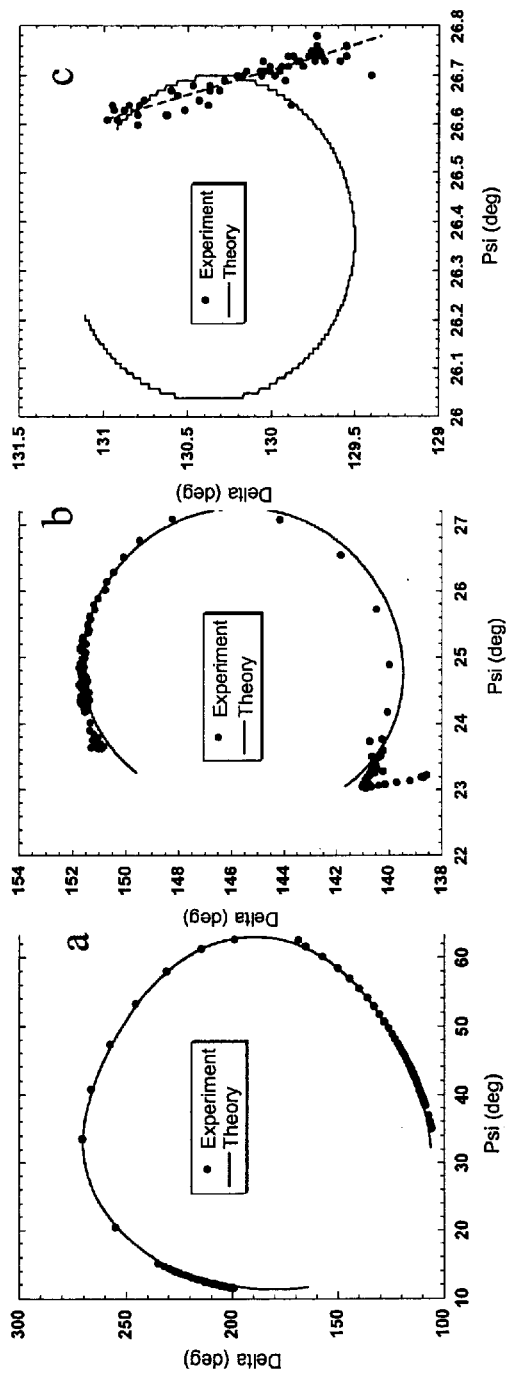
FIG. 4 are $\Psi/\Delta$ diagrams representing experimental data (points) and results of simulation (lines). Adsorption of toluene in the porous SOG film without barrier (designated as "a"), with 30 nm Ta(N) (designated as "b") and with 60 nm Ta(N) (designated as "c"). The dashed line on graph (c) corresponds to the toluene adsorption on top of barrier.

The physical idea of the barrier evaluation by EP is similar to PALS. To evaluate a barrier, PALS examines escape of Ps through voids in the barrier. EP examines penetration of molecules through the voids and their adsorption in the low-k film. FIG. 4 shows experimental results obtained with a 50% porous SOG low-k film. The pore diameter was close to 5 nm. The Ionized—Physical Vapor Deposition TaN films with various thickness were deposited on top of low-k films. The $\Psi/\Delta$ diagrams represent experimental data and theoretical calculations for the toluene adsorption in the porous film. A 2-layered ellipsometric model was used for the simulation of the barrier/low-k stack. As a reference, FIG. 4a shows experimental data and a theoretical curve for the toluene adsorption in a non-capped porous film. A good agreement between the experimental data and results of calculation suggests that toluene uniformly filled pores in the low-k film. Similar results obtained with the wafer 2 suggests that 30 nm thick barrier still contains voids (FIG. 4b). Only samples with 60 nm of Ta(N) cap showed no condensation in the pores (FIG. 4c). It was established that the TaN barrier becomes non-porous at the thickness between 40 nm and 60 nm. The PSD of the pristine low-k film and with 10 nm Ta(N) cap are almost the same, only the PSD of 30 nm thick Ta(N) is slightly shifted towards smaller pore radius. This shift can be explained by decrease of the pore size in the capping layer. When a 10 nm thick Ta(N) film was deposited on top of SiOCH film, no adsorption of toluene in the porous film was observed regardless the pore size. Therefore, the necessary barrier thickness is defined not only by pore size but also by chemical affinity of the low-k film and barrier. Optical characteristics and thickness of the barrier and low-k films can also be characterized. This characterization allows getting information related to modification of low-k dielectric during the barrier deposition. The barrier thickness measured by EP is in good agreement with data obtained a four-point probe measurement of the TiN resistance.

Figure 5:
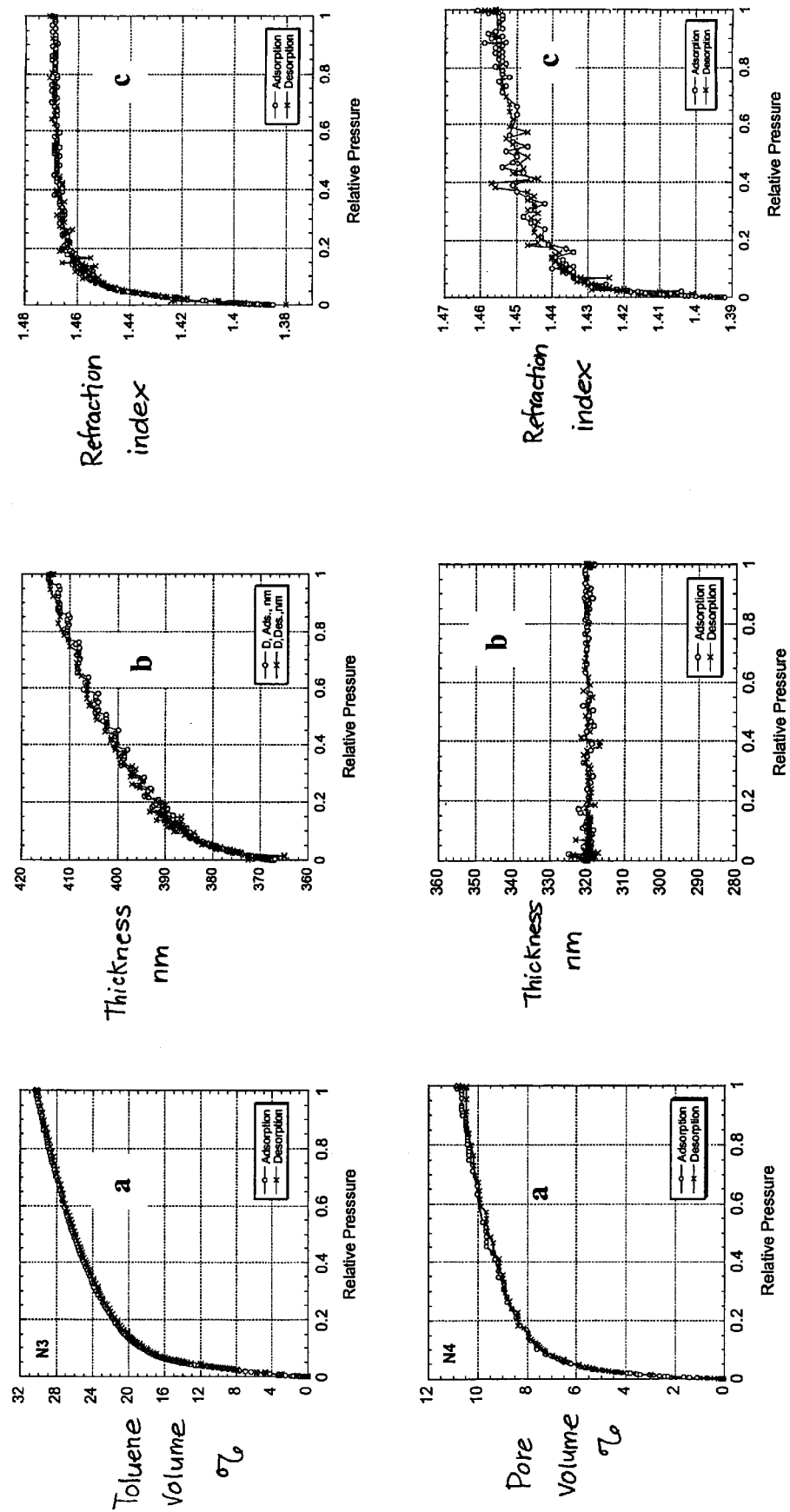
FIG. 5 shows in the second column for two films (each row one film) the thickness of the film versus the relative pressure and in the third column the refractive index (or refraction) versus the relative pressure. The change of the refractive index for relative pressure value above a certain threshold (here 0.2) indicates the possibility of having pore-killers. The change of the thickness of the film as found in row 1 indicates the swelling of the film. The substantial constant value of the thickness in row 2 leads to the conclusion that this film must have pore-killers.

FIG. 5a shows the toluene adsorption/desorption isotherms in two SiCOH films deposited at different conditions. These films are microporous because the isotherms have the main slope at the relative pressure below 0.2 and do not have a hysteresis loop. Most of pores have a closed radius: 0.7 and 0.65 nm. However, an insignificant slope (increase of the adsorbate volume) is observed at P/Po>0.2. The increase of the adsorbate volume at P/Po>0.2 suggests that these films may contain some amount of larger pores or they are swelling during the adsorption. To distinguish between these mechanisms, one can analyze the change of the film thickness and refractive index during the adsorption (FIGS. 5b,c). One can see that thickness of the film N3 is increasing at P/Po>0.2 while the refractive index is constant. Therefore this film is swelling. Thickness of the film N4 is constant but a remarkable change of the refractive index is observed at P/Po>0.2. This is related to filling of the pores with size larger than 2 nm. Most of the pores in these films have radius 0.65–0.7 nm and the thickness of the diffusion barrier will be optimized from this point of view. Therefore, the large pores present in this film are device "killers" because the diffusion barrier on top of them will have voids.

A phenomenological explanation of these conclusions is the following. If a material is porous, the change of the refractive index during the adsorption is related to the replacement of air in the pores (n=1) by a liquid adsorbtive (n=1.49 in the case of toluene). Therefore, the change of the refractive index at a constant film thickness is related to the pore filling. If a non-porous film is swelling during the adsorption, the change of thickness is observed, but the change of the refractive index depends only on difference between refractive indices of the film skeleton and liquid adsorptive. In the case of the film N3 the skeleton refractive index was very close to the toluene refractive index (1.5 and 1.49). Therefore, penetration of toluene to the film skeleton (at P/Po>0.2) cannot change refractive index of the film. It was observed that if the film skeleton has a larger refractive index than the adsorptive, the refractive index is decreasing during the adsorption.

Ellipsometry provides precise measurements of the film thickness and refractive index. Therefore, such kind of analysis allows recognizing presence of pores "killers" in porous low-k films. The change of the refractive index versus relative pressure allows calculation of the PSD in low-k films without uncertainties caused by the film swelling. There are several types of low-k films that are swelling during the adsorption. Typical representatives of these films are organic polymers and some CVD SiOCH films.

Table I summarizes the properties of IPS and XLK films measured by different methods. Two of them are sorption porosimetry (EP and nitrogen BJH porosimetry) and the others are radiation beam-based (SANS/XRR and PALS). Bulk specimens are used only in the BJH porosimetry—i.e., it is a film-destructive method. The BJH porosimetry was used as a standard technique for the porosity characterization. The average pore diameters show good agreement with the EP data, including the inversion of pore diameters of RR18 and RR20. Cumulative pore volumes are 0.98, 0.88, 0.70, and 0.35 (ml/g) for RR18, RR20, RR22 and RR25, respectively, and show consistent agreement with the EP data and the change of dielectric constant. $N_2$ sorption porosimetry is not capable of detecting inaccessible (closed) pores because the adsorptive vapor is not accessible to the closed pores. A unique feature of EP is that the amount of closed pores can be determined with a multiangular or SE measurements arrangement assuming a dielectric model wherein the film consists of solid part+open porosity filled with adsorptive+closed pores. It is found that the pore connectivity, the ratio of open porosity to total porosity increases from 86% (RR25) to 97%(RR18), as k decreases. The determined full porosity is seen to consistently increase as the dielectric constant decreases. In the radiation beam-based porosimetry techniques—SANS/XRR and PALS—the primary beam interacts with pores and/or wall material and carries the information about the pore structure. The pore size is extracted from the measured signal, assuming pore geometry and physical interaction between the beam and pore. In SANS/XRR experiments, Rutherford Backscattering Spectrometry (RBS) and Forward Recoil Elastic Scattering (FRES) are also employed, and film thickness, wall density, overall film density, porosity, average pore chord length (pore size), and elemental composition are characterized. Film thickness data calculated from XRR are in good agreement with the data from EP, where the difference is within 4%.

The PALS data are deduced using an infinitely long square channel pore model, where the pore size is the side length corresponding to a tubular pore diameter. The pore size increases with decreasing k, and the values are very similar to those obtained by other techniques. In all these films the pores are found to be nominally fully interconnected. The instrumental methods employed in this study are based on different physico-chemical principles. The pore sizes are not directly acquired from the measurements. In order to determine the pore size and porosity, it is necessary to transform the raw data by assuming an appropriate model that takes into account pore structure and pore-probe interaction. That is, the results can be highly model dependent. Sorption porosimetry reflects pore surface geometry and SANS reflects spatial density of scattering bodies, either voids or particles. PALS is more related to the volume of void elements. For these reasons, we must emphasize that perfect agreement cannot be obtained. Besides the above points, it can be safely said that successful agreement is obtained. The difference in pore size between the results for the IPS films is not significant. The only smaller pore size was obtained by SANS/XRR in the XLK film. It is also found that the spread of pore size increases with average pore size. This is a general feature of the traditional SOG films and was observed in different SOG films. Table 2 shows comparative characterization of different non-destructive techniques. Below is an analysis of problems and limitations of the each method that can appear during the analysis of porous films is provided. EP needs knowledge of the refractive index of the dense prototype to calculate the full porosity. This value is available for most of low-k films or can be estimated if the chemical composition is known. If the porous film is completely unknown, EP may have problems with calculation of full porosity, and as a result, with calculation of the film density and pores interconnectivity. EP is not able to measure the size of closed pores. The size of closed pores can be measured by etching the top dense layer (if the film is capped). Both PALS and PAS generally are able to estimate the film porosity by comparison of Ps annihilation inside pores and in vacuum. All positron annihilation states contribute to a PALS spectrum. If the intensity of a given component is known, one can conclude that the fraction of the long o-Ps lifetime is equal to the porosity fraction. However, Ps annihilates after a limited number of collisions with pore wall. Therefore, if the low-k film contains pores with long and narrow "bottlenecks", the Ps movement through these necks is limited [10]. In this case, some Ps is not able to escape to vacuum due to the large number of collisions—enough for the annihilation inside the necks. Therefore, these open pores behave as closed pores. As a result, these methods will have a tendency to underestimate the open porosity and degree of pore interconnectivity. For instance, EP showed that toluene filled all pores in the MSSQ based films while PALS showed that Ps no not escape from the pores when the films were prepared with relatively low porogen concentration [20]. It is necessary to mention that the time of toluene adsorption is comparable with the real technological procedures used for post dry-etch cleaning. Therefore, if toluene penetrates into the pores, one can be sure that these pores are open for the cleaning solvents. The radiation scattering techniques (SANS and SAXS) are able to derive the mean pore size. The bi- or multi modal pores cannot be distinguished. These methods need to be combined with XRR measurements to determine the film density and calculate porosity.

Generally, SAXS is also able to derive the total surface area and porosity in the bulk materials. However, this procedure is hardly applicable for thin films because the total pore volume and surface area are too small. This is the reason why this SAXS option has not been realized so far. SAWS measure the film density and Young's Modulus. Porosity calculations need knowledge of the skeleton density as well. This method provides a unique possibility of non-destructive measurement of Young's Modulus. Taking into account this advantage and SAWS compatibility with the EP tool, we recently showed that such type of combination is extremely useful for evaluation of low-k dielectrics.

Advanced non-destructive methods, such as ellipsometric porosimetry (EP), small-angle neutron and X-ray scattering (SANS and SAXS) combined with specular X-ray reflectivity (XRR), positron annihilation spectroscopy (PALS, PAS), have been developed to characterize the pore size and PSD of thin porous films. These methods are based on different physico-chemical principles and the pore sizes are not directly acquired from the measurements. In order to determine the pore size and porosity, it is necessary to transform the raw data by assuming an appropriate model that takes into account the pore structure and pore-probe interaction. Sorption porosimetry reflects pore surface geometry, SANS and SAXS reflects spatial density of scattering bodies, either voids or particles. PALS is more related to the volume of void elements. From a methodology point of view, we conclude that any methods described here are appropriate for characterizing porosity. However, it should be recommended that the method chosen must assess a parameter related as directly a possible to phenomena involved in the application of the porous film. The selected method preferably has to use physical phenomena similar or close to those involved during the practical application (i.e. adsorption methods are useful to get a direct information related to the porous film behavior during the strip/cleaning and other chemical procedures involved in technological steps). EP is a modification of adsorption porosimetry. This method allows the measurement of PSD at room temperature in thin films directly deposited on Si or any smooth solid substrate. A small surface area is sufficient to carry out this analysis, making the method well suited for the microelectronics industry. EP is more informative than the traditional microbalance porosimetry: the relative volumes of close pores and structural changes during the adsorption and desorption processes can also be analyzed. EP can be used for evaluation of diffusion barriers, change of pore size due to the film swelling and to recognize pores "killers" in low-k films. Ellipsometry is a simple and traditional instrumentation has been used in ULSI technology. It makes possible to consider EP as the most promising candidate to be employed for in-line monitoring of low-k dielectric films in the industrial environment.

TABLE I

Summary of PSD analysis.

| Sample (IPS) | K | Thickness (nm) EP SXR | Porosity (%) EP SANS/XR | | Characteristic Pore Size (Å) EP PALS | BJH | SANS |
|---|---|---|---|---|---|---|---|
| RR18 | 1.8 | 265 ± 1<br>265 ± 1 | 53 ± 4 | 37 ± 7 | 84 ± 2<br>82 ± 9 | 70 | 62 ± 8 |
| RR20 | 2.0 | 418 ± 1<br>424 ± 1 | 45 ± 2 | 33 ± 6 | 90 ± 3<br>73 ± 5 | 92 | 61 ± 6 |
| RR22 | 2.2 | 427 ± 1<br>424 ± 1 | 39 ± 4 | 26 ± 5 | 57 ± 2<br>57 ± 2 | 63 | 50 ± 4 |
| RR25 | 2.5 | 410 ± 1<br>427 ± 1 | 26 ± 4 | 20 ± 7 | 31 ± 4<br>39 ± 2 | 33 | 27 ± 3 |
| XLK2.0 | 2.0 | 615 | 52 | — | 42<br>42 | 40 | 22 |
| XLK2.5 | 2.5 | 710 | 21 | — | 28<br>27 | — | — |
| X* | — | 420 | 34 | — | 20<br>20 | — | — |

X* is Dow Corning Next Generation Porous Dielectric.

TABLE 2

Comparative characteristics of instrumentation used for the non-destructive characterization of porous low-K dielectric films.
●—proven option;
*—an option that has been realized but may have problems.

| Problem | SAXS 1 | SANS 2 | XRR 3 | PALS 4 | PAS 5 | EP 6 | SAWS 7 | SE 8 |
|---|---|---|---|---|---|---|---|---|
| Open pore size | ● | ● | * | | ● | ● | | |
| Closed pore size | ● | ● | | ● | ● | | | |
| Full porosity | | | * | * | * | * | * | * |
| Closed | | * | | * | * | * | | |

TABLE 2-continued

Comparative characteristics of instrumentation used for the non-destructive characterization of porous low-K dielectric films.
●—proven option;
*—an option that has been realized but may have problems.

| Problem | SAXS 1 | SANS 2 | XRR 3 | PALS 4 | PAS 5 | EP 6 | SAWS 7 | SE 8 |
|---|---|---|---|---|---|---|---|---|
| pore volume | | | | | | | | |
| Open pore volume | | * | | * | ● | ● | | |
| Interconnectivity | | * | | | ● | ● | ● | |
| Skeleton properties | ● | | | | | ● | | * |
| Bi-modal pores size | | | | | ● | ● | ● | |
| PSD | | | | | ● | ● | ● | |
| Barrier evaluation | | | | | ● | ● | ● | |
| Film density | | | ● | | * | | ● | * |
| Film thickness | | | | | | | ● | ● |
| Refractive index | | | | | | | ● | ● |
| Spec. surface area | | * | | | | ● | | |
| Young's Modulus | | | | | | | ● | ● |

Determination of the Young's Modulus of Film

In a second aspect of the invention, a method for determining the Young's modulus of a film, placed in a pressurized chamber, is described comprising the steps of determining via ellipsometric measurements a set of data of the thickness of the film versus said pressure in said chamber; and calculating the Young's modulus of said film from said set of data.

Alternatively formulated this aspect of the invention is a method for determining the Young's modulus of an element which is positioned in a pressurizable chamber, filled with a gaseous substance, said method comprising the steps of performing ellipsometric measurements on said element for pressures less than the equilibrium vapor pressure of said gaseous substance, to determine data on the film thickness as a function of said pressure; and determining the Young's modulus from said data.

In an embodiment of the invention, a method as recited in the second aspect of the invention is described wherein said film is a porous film. In a further embodiment of this second aspect of the invention, a method as recited in any of the embodiments is disclosed wherein said film is a porous film used as insulating layer in semiconductor processing.

In an embodiment of this second aspect of the invention, a method as recited in any of the previous embodiments is disclosed wherein said first step is performed according to patent application WO 00/1299 and issued U.S. Pat. No. 6,319,736.

In an embodiment of this second aspect of the invention, a method as recited in any of the previous embodiments is disclosed wherein said method is used for quality testing said film. In a further embodiment thereof said quality testing method comprises the step of accepting or rejecting the film.

In an embodiment of this second aspect of the invention, a method as recited in any of the previous embodiments is disclosed wherein said method is used as part of an on-line process control method for controlling the fabrication process of said film In a further embodiment thereof said process control method comprising the steps of changing the parameters of the film fabricating process.

A method for determining the Young's modulus of an element formed on a substrate, said substrate being positioned in a pressurizable chamber at a predetermined chamber temperature, filled with a gaseous substance is described, said method comprising the steps of:

performing ellipsometric measurements on said element for pressures less than the equilibrium vapor pressure of said gaseous substance at said chamber temperature, to determine data on the film thickness as function of said pressure; and determining the Young's modulus from said data.

In an embodiment, one can fit the experimental curve describing the change of the film thickness versus relative pressure, and combine the fit parameters with the molecular volume of the gaseous substance.

From ellipsometric measurements the film thickness can be evaluated. Insignificant and reversible film shrinkage during the capillary condensation is an elastic response to capillary forces that depends on the Young's Modulus of the porous film. The calculation of E-Modulus of thin porous film using EP data is based on the following:

The chemical potential governing capillary condensation can be expressed in terms of the microscopic capillary pressure, which is defined as difference between the pressure in gaseous and liquid phases across the meniscus:

$$\pi_c = \pi_g - \pi_l \quad (2)$$

According to the Young-Laplace equation with $\gamma$ the surface tension of the liquid adsorptive and r is the mean radius of curvature of the liquid-vapor interface:

$$\pi_c = 2\gamma/r \quad (3)$$

The capillary pressure of the condensed adsorptive is always positive and results to microscopic compressive forces in the film that are large enough for film shrinkage. The capillary stress in the porous material caused by $\pi_c$ may exceed $10^{th}$ MPa if the pore radius is smaller than 20 nm. The pore size calculations are based on the Kelvin equation:

$$\frac{2}{r} = -\frac{RT}{\gamma V_L \cos\theta} \ln\left(\frac{P}{P_0}\right) \quad (1)$$

where $V_L$ is the molar volume of the liquid adsorptive, respectively. $\theta$ is the contact angle of the liquid adsorptive. $\theta$ is the vapor pressure above said liquid-vapor interface. Po is the vapor pressure above a flat interface. Combination of the Kelvin and the Young-Laplace equations (1,3) gives $$\pi_c = \ln\frac{P}{P_0} \cdot \frac{RT}{V_L} \quad (4)$$

The equation (4) shows that molecular volume $V_L$ of the condensed liquid and relative pressure above a meniscus are responsible for the pressure gradient between liquid and gas phase. The value of relative pressure P/Po corresponding to the maximum shrinkage depends on pore radius and surface tension of the liquid. Change of the film thickness (degree of shrinkage) is equal:

$$d = d_0(1 - \pi_c/E) = d_0 - k\ln\frac{P}{P_0} \qquad (5)$$

where $k=d_o RT/V_L E$. To calculate the E value, one can fit the experimental curve describing the change of the film thickness versus relative pressure, to find k and $d_o$ and to use the following formula obtained by combination of equations (4) and (5):

$$E = \frac{d_0 RT}{kV_L} \qquad (6)$$

It is important to mention that the only molecular characteristic of the adsorptive needed for calculation of Young's Modulus from EP data is the molecular volume.

Figure 6:
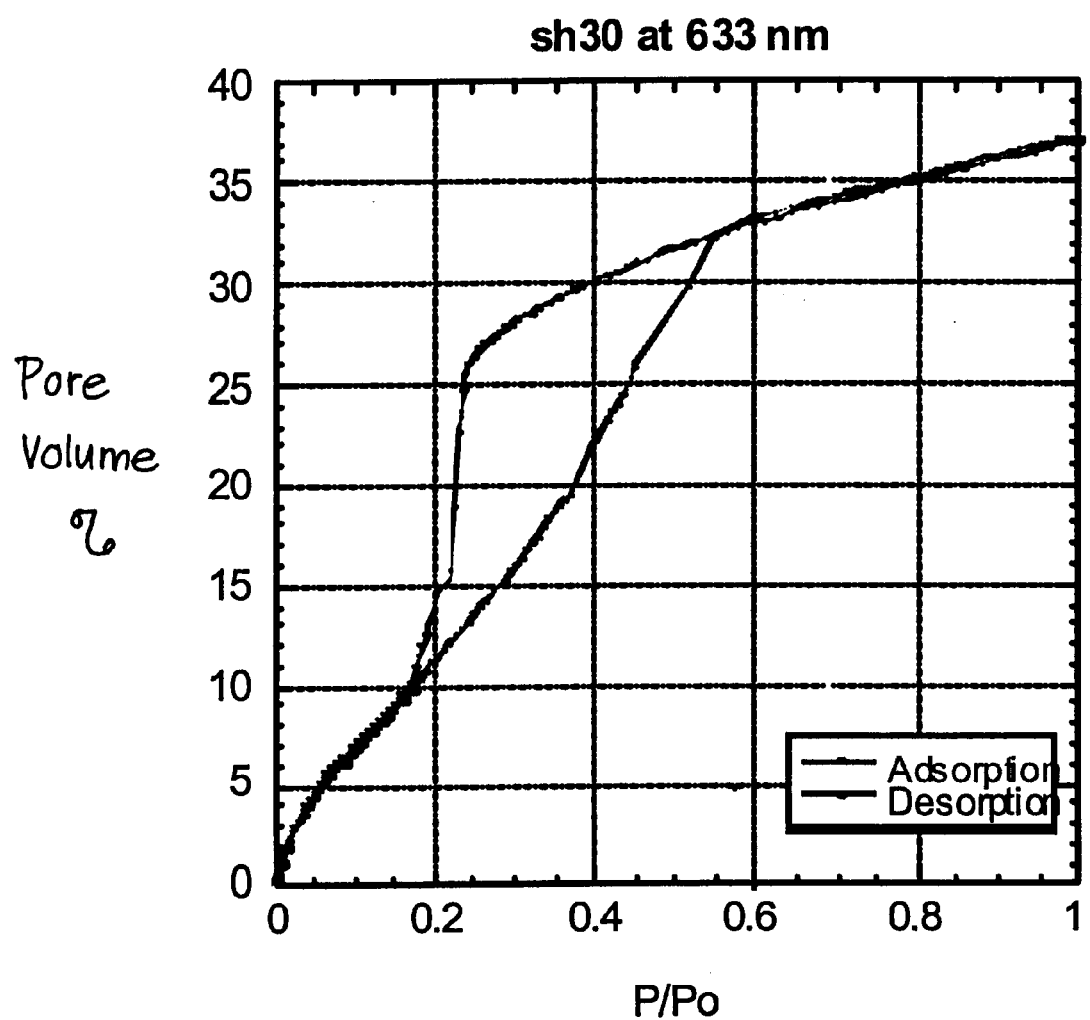
FIG. 6 is a graph of the adsorption/desorption isotherm of toluene vapor in porous MSSQ based low-k film prepared with 20% of porogen loading.
Figure 8:
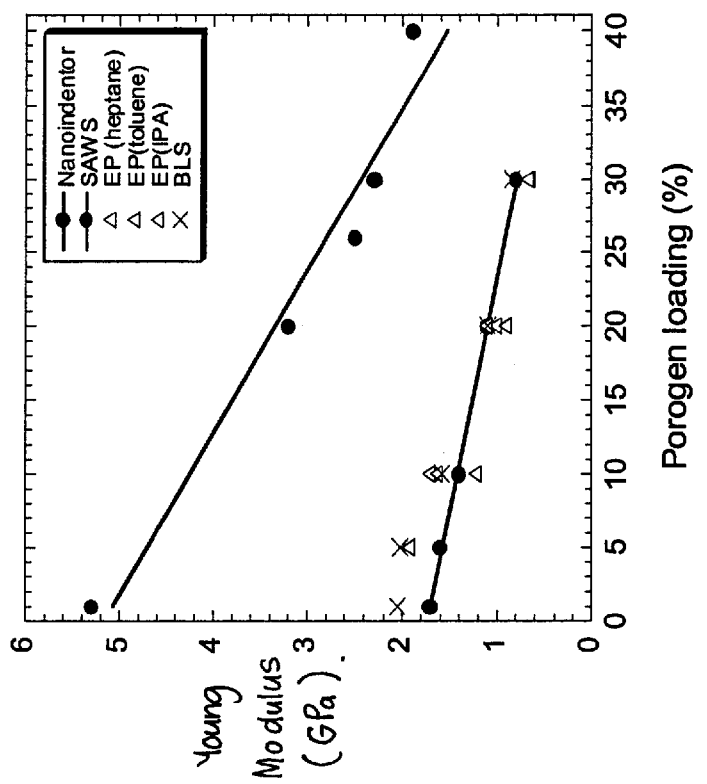
FIG. 8 is a graph of comparison of E-values determined by Ellipsometric Porosimetry, Nanoidentation, Surface Acoustic Wave Spectroscopy and Brillouin Light Scattering.
Figure 7:
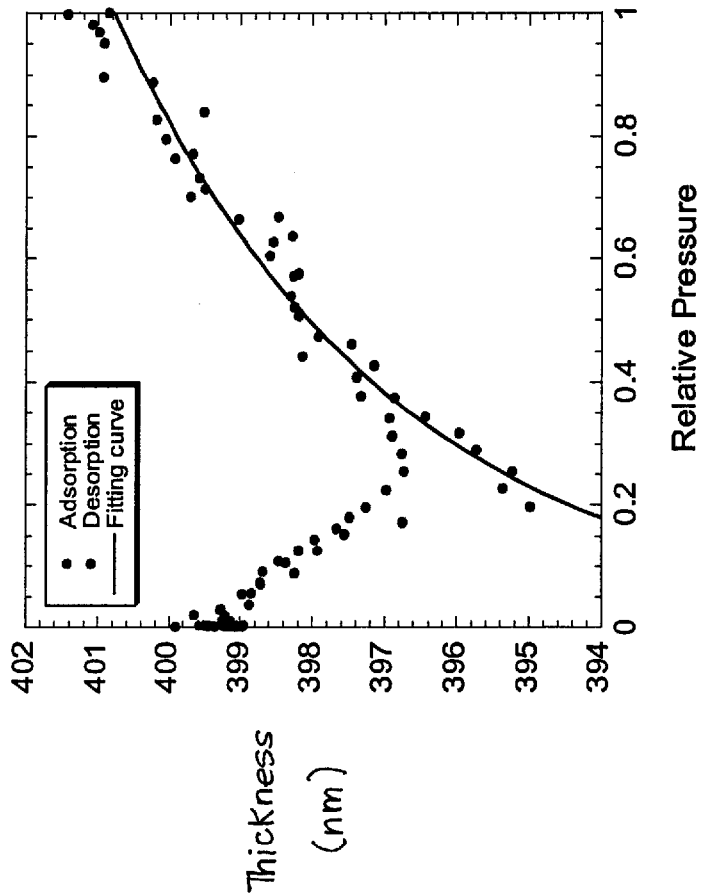
FIG. 7 is a graph of change of the film thickness during the toluene adsorption and desorption and fitting of the experimental curve by equation (6). The fit parameters are exploited for E modulus determination.

The samples inspected were porous MSSQ based low-K films. All the films were 1 μm thick and were prepared with porogen concentration 1–30% on Si (001) wafers. EP showed a bi-modal PSD; a 16% of the porosity is due to intrinsic micropores (<2 nm diameter) while the porosity increase is due to an increasing number of mesopores, having an almost constant diameter 3.5 nm (equal to porogen particle size) over the porosity range measured [M. R. Baklanov, C. Jehoul, C. M. Flannery, K. P. Mogilnikov, R. Gore, D. Gronbeck, G. Prokopowicz, C. Sullivan, Y. You, N. Pugliano and M. Gallagher. Proc. 2001 MRS Advanced Metallisation Conference (AMC), Montreal, Canada.]. Mechanical properties of these films were preliminary evaluated by NI, SAWS and BLS and therefore they are convenient for comparative testing. FIG. 6 shows adsorption/desorption isotherm (a) and change of the film thickness during the toluene adsorption and desorption (b). Degree of shrinkage of these films didn't exceed 1.5–2% of the film thickness that is negligible from the point of view of the porosity evaluation using the standard EP software. The final film thickness corresponds to the complete filling of all the pores at P/Po=1 when the liquid surface inside the pores do not form a concave meniscus. Decrease of the toluene pressure first results in formation of the meniscus curvature. The adsorbate volume is still almost equal to the maximum pore filling (pore volume). Minimum film thickness corresponds to the relative pressure when the curvature radius of the meniscus becomes minimal (just before emptying of largest pores has begun). Behavior of the film thickness during the adsorption (from the empty pores to the minimum film thickness) is more complicated for calculations because some large pores inside the film can be filled non-uniformly and with delay. This is the reason why degree of shrinkage during the adsorption is less than during desorption. Therefore, it is more convenient to use the change of the film thickness in the range between P/Po corresponding to the minimum film thickness and P/Po=1. The best fit of the experimental curve by the equation (5) allows determination of the coefficient k and to use it for calculation of the Young's Modulus. FIG. 7 shows E values of the low-k films prepared with different porogen concentrations. A good agreement between EP Young's Modulus and data obtained by SAWS and BLS is obvious. Thus, these data demonstrate that EP data can be used for the calculation of E values simultaneously with evaluation of pore structure. Referring to FIG. 8, there is shown a graph of comparison of E-values determined by Ellipsometric Porosimetry, Nanoindentation, Surface Acoustic Wave Spectroscopy and Brillouin Light Scattering.

Figure 9:
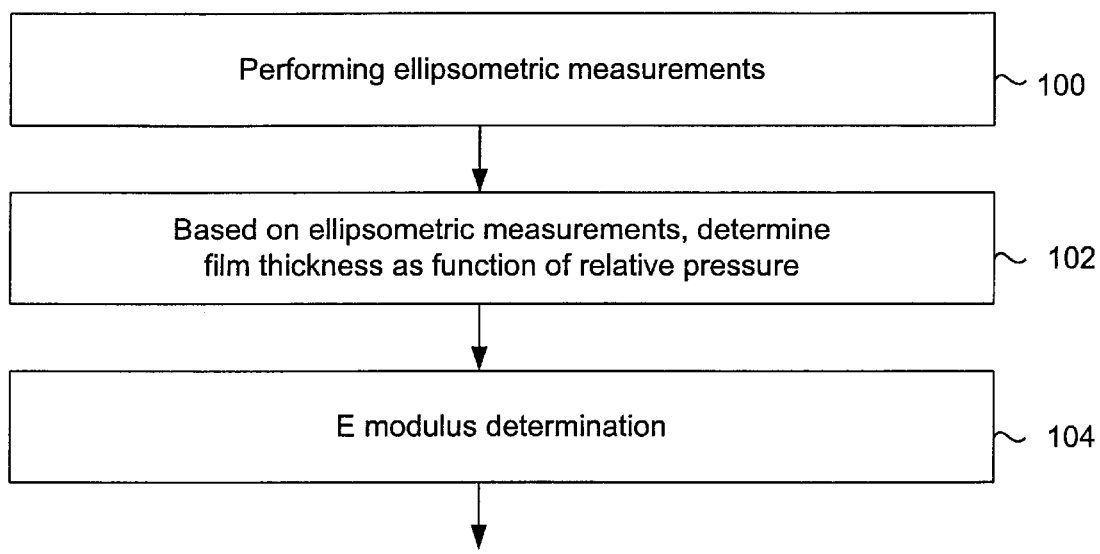
FIG. 9 shows a flowchart of the second aspect of the invention, for determining E modulus.

FIG. 9 shows a flowchart of the second aspect of the invention, for determining E modulus. In a first step (100) ellipsometric measurements are performed. Thereafter the film thickness as function of relative pressure is determined in a subsequent step (102) from the obtained data. In a final step (104), the E modulus is determined.

Figure 10:
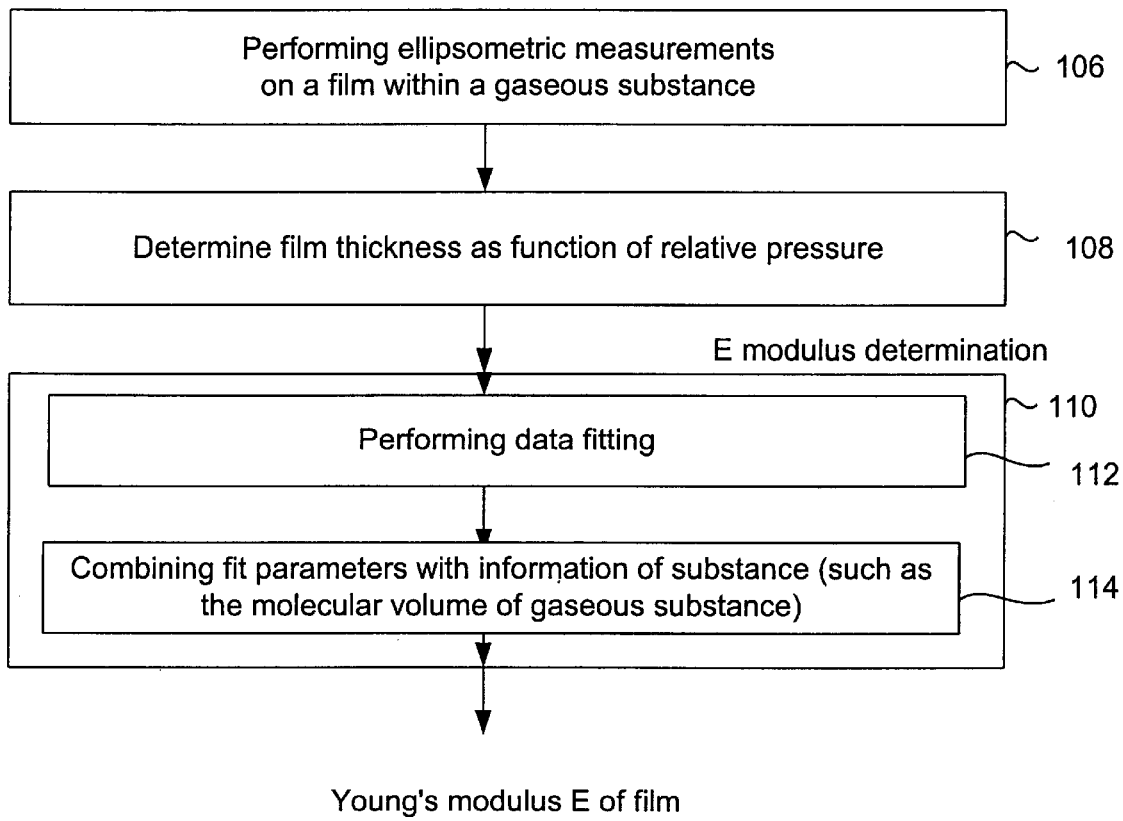
FIG. 10 shows an embodiment of said second aspect by indicating a two-step E modulus determination.

FIG. 10 shows a flowchart of an embodiment of said second aspect. Again in a first step (106), ellipsometric measurements are performed on a film in a gaseous substance. Thereafter the film thickness as function of relative pressure is determined in a subsequent step (108) from the obtained data. The E-modulus determination step (110) comprises a first substep (112) of performing data filling on the thickness/pressure data and a second substep (114) wherein the obtained fit parameters are combined with information of the substance such as the molecular volume.

Figure 11:
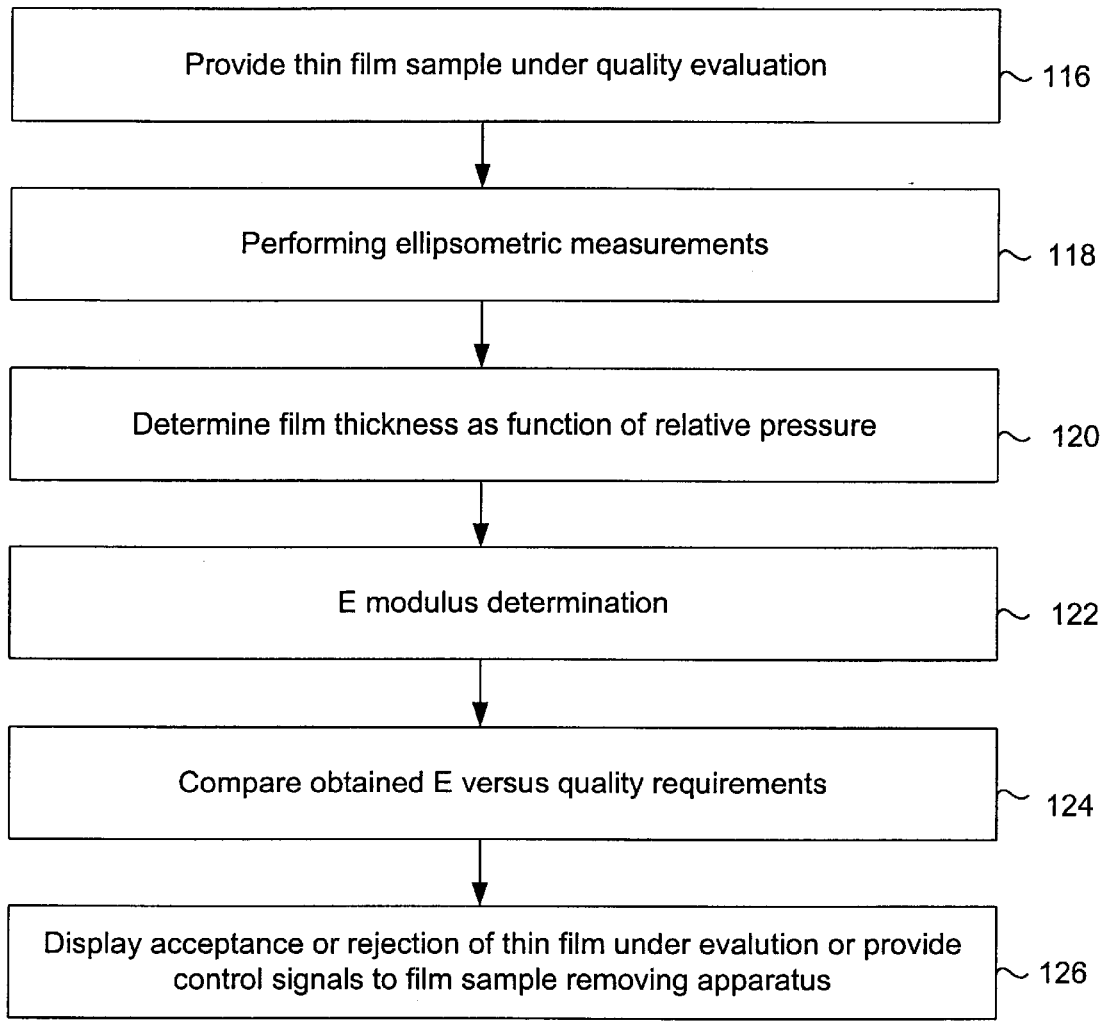
FIG. 11 shows how said second aspect of the invention is used within a quality control environment.

FIG. 11 shows how said second aspect of the invention is used within a quality control environment by indicating a step (116) of providing a sample under quality evaluation in a measurement set-up (for instance placing said sample within the pressurized chamber needed for ellipsometric measurements), followed by the steps of performing said measurements (118), determining (120) thickness/pressure data and therefrom computing the E-modulus (122), followed by the evaluation step (124) wherein the obtained E modulus is compared with the quality requirements, for instance formulated as a range and finally (126) a concluding step wherein acceptance or rejection is either displayed or invokes signals for removing the sample from the production line.

Figure 12:
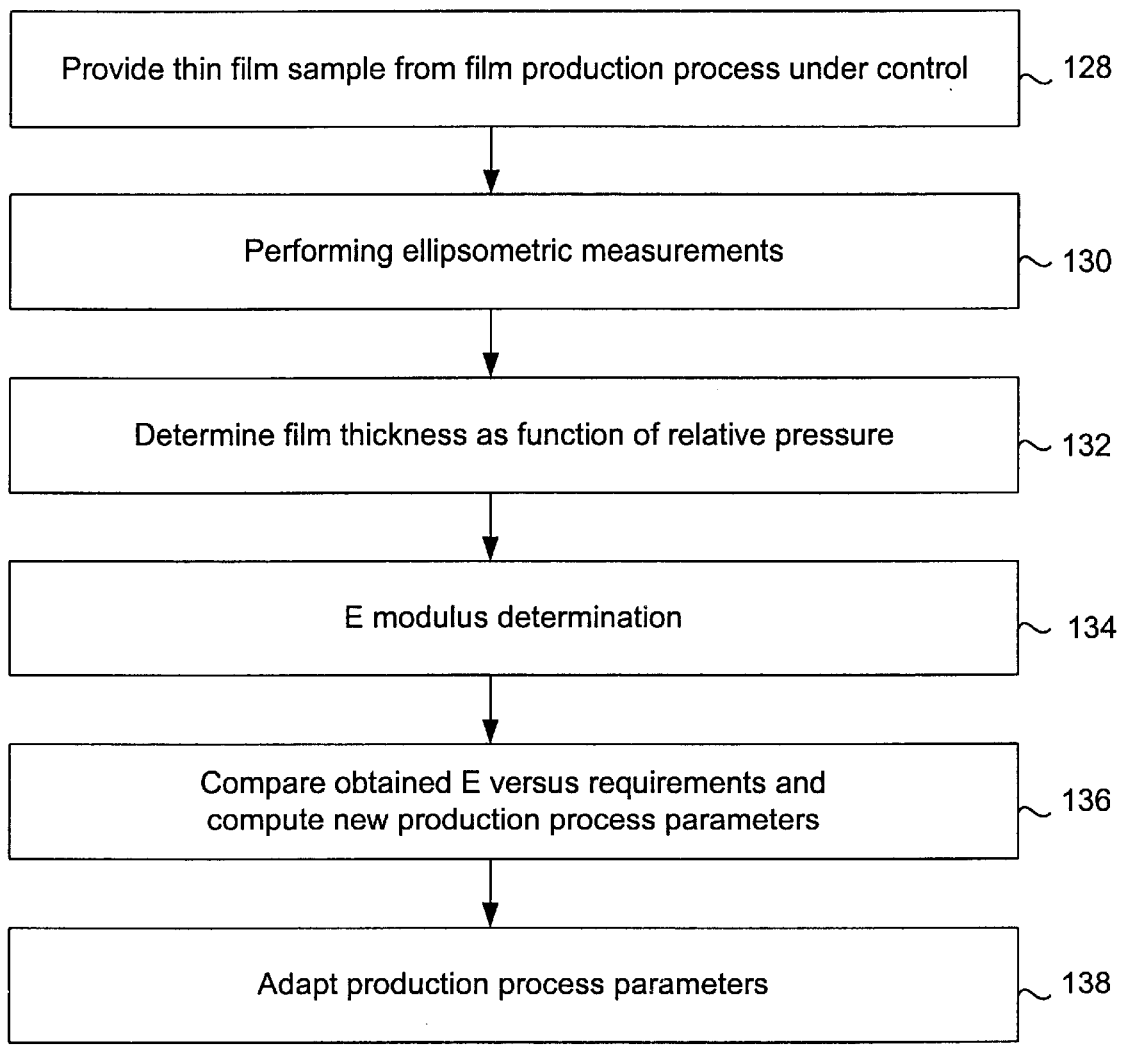
FIG. 12 shows how said second aspect of the invention is used within a process control environment.

FIG. 12 shows how said second aspect of the invention is used within a process control environment by again indicating a step (128) of providing a sample in a measurement set-up, followed by the steps of performing measurements (130), determining (132) thickness/pressure data and therefrom computing the E-modulus (134), followed by the evaluation step (136) wherein the obtained E modulus is compared with the quality requirements and the difference are used for computing new production process parameters like anneal temperatures, duration of anneal steps and finally (138) a step of actual adaptation of the production process parameters (in an automated fashion) is performed.

Figure 13:
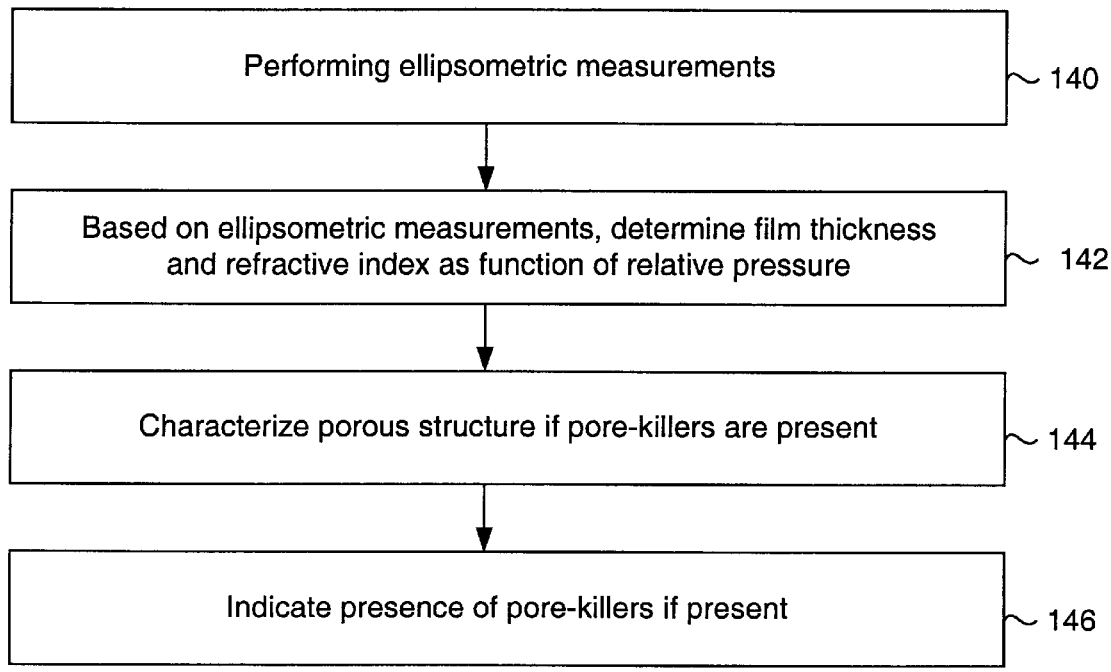
FIG. 13 shows a flow chart of said first aspect of the invention.

FIG. 13 shows a flow chart of said first aspect of the invention. In a first step (140) ellipsometric measurements are performed on a film in a gaseous substance. Thereafter the film thickness and refractive index as function of relative pressure is determined in a subsequent step (142) from the obtained data. Then the porous structure is characterized (144), in the sense that determination of the presence of pore-killers is done, followed by an indication step (146), for instance displaying the estimated amount of pore-killers.

Figure 14:
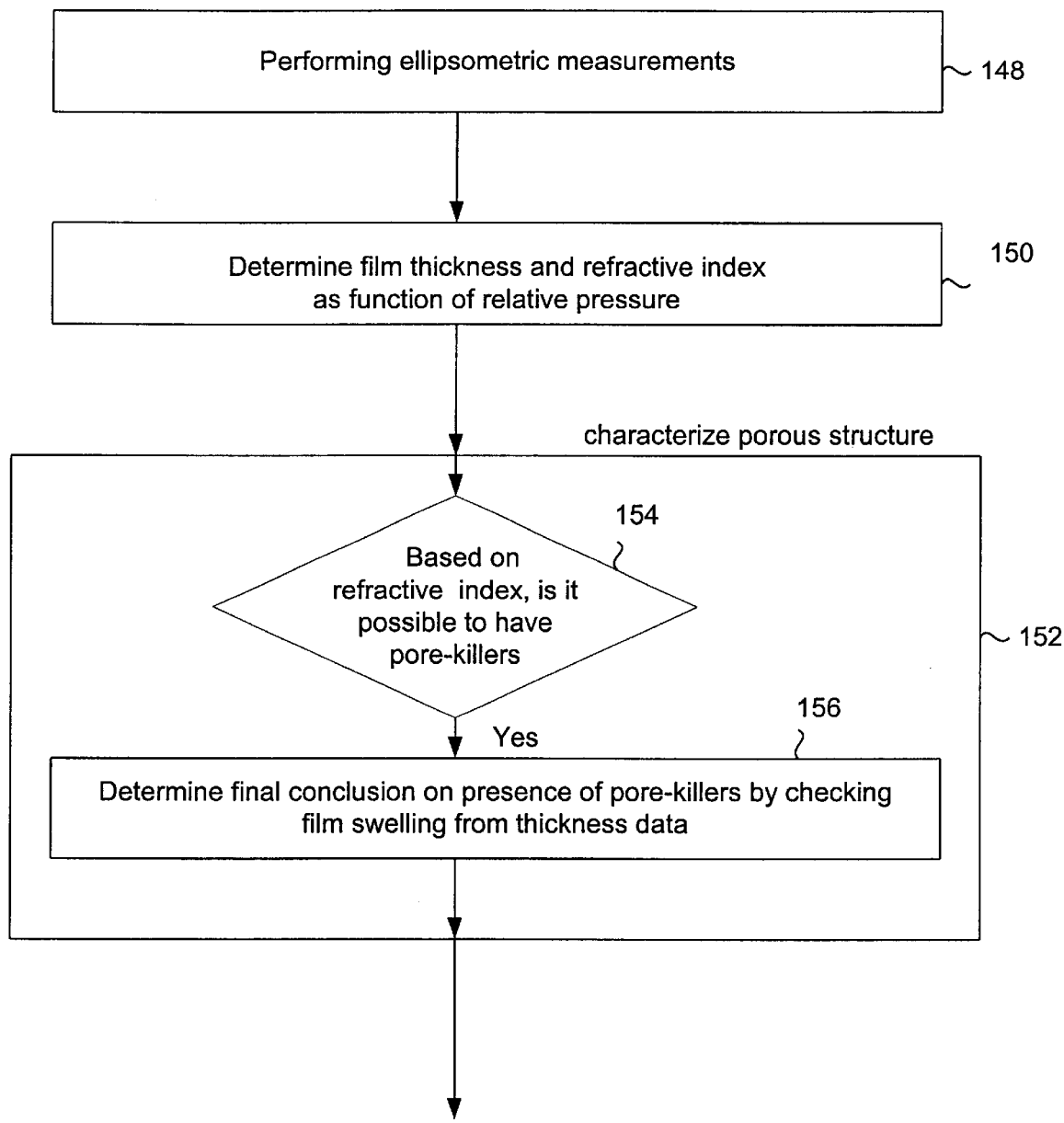
FIG. 14 shows a two-step characterization of the porous structure.

FIG. 14 shows an embodiment of said first aspect of the invention, indicating that besides performing of ellipsometric measurements (148) and thickness/refractive index data (150) the porous structure characterization step (152), comprising two substeps, wherein in a first substep the possibility of having pore-killers is determined (154) by using refractive index data, followed by a final conclusion step (156), using thickness data.

Figure 15:
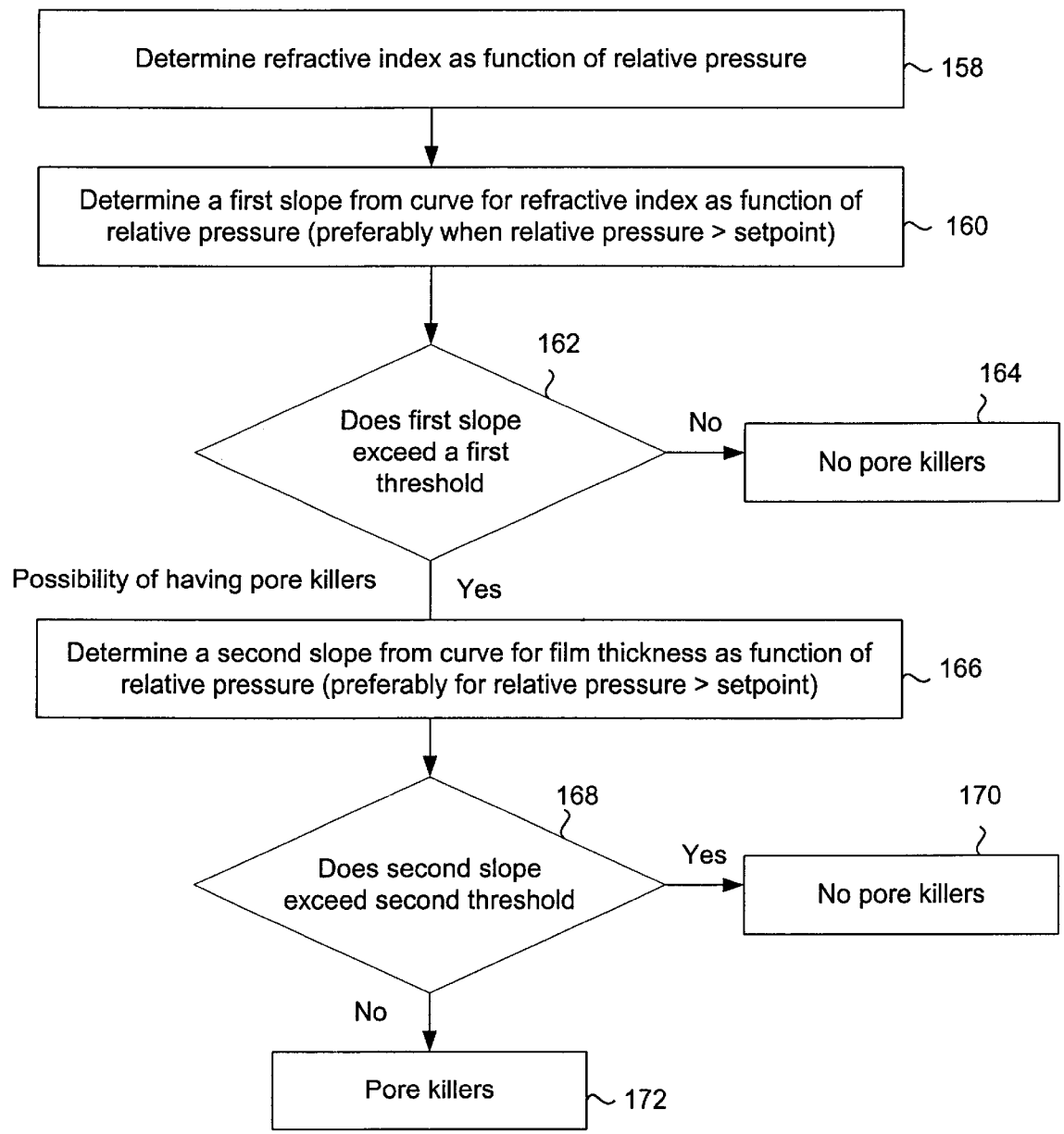
FIG. 15 shows a decision chart on how a final conclusion on the presence of pore-killers is reached.

FIG. 15 shows a decision chart on how a final conclusion on the presence of pore-killers is reached. After performing of ellipsometric measurements and determining thickness/refractive index data (158), the porous structure characterization step, has a step of determining a first slope (160) from the refractive index curve for a range of relative pressures. This can be either after determining a smooth curve through the data points or directly from the data. Then a decision step (162) comparing said first slope with a first threshold is performed. Conclusions on the possibility of having pore-killers are drawn. If no, one can conclude that no pore-killers (164) are present. In the other case, there is a possibility of having pore-killers. A second slope determination step (166) now on the thickness curve again for a range of relative pressures is executed, again either indirectly or directly on the data, followed by a second decision step (168), drawing final conclusions of the presence of pore-killers. The conclusions of said decision steps are indicated (164, 170, 172).

The methods may be performed using a processor in combination with a memory device (such as a computer). The processor may comprise a microprocessor, a microcontroller, or any device which performs arithmetic, logic or control operations. The memory device may include non-volatile memory devices such as a ROM and/or volatile memory devices such as a RAM.

The software can be represented as a sequence of binary bits maintained on a computer readable medium described above (such as a program storage device readable by a machine and encoding a program of instructions for executing a method). The computer readable medium may include magnetic disks, optical disks, and any other volatile or (e.g., Random Access memory ("RAM")) non-volatile firmware (e.g., Read Only Memory ("ROM")) storage system readable by the processor. The memory locations where data bits are maintained also include physical locations that have particular electrical, magnetic, optical, or organic properties corresponding to the stored data bits. The software instructions are executed as data bits by the processor with a memory system causing a transformation of the electrical signal representation, and the maintenance of data bits at memory locations in the memory system to thereby reconfigure or otherwise alter the unit's operation. The executable software code may implement, for example, the methods as described above.

In one embodiment, the program storage device may be readable by a machine and encoding a program of instructions for executing a method. The method may comprise the steps of: loading data (the data being obtained by performing at least one elipsometric measurement on a film formed on a substrate, said substrate being located in a pressurizable chamber filled with a gaseous substance at a pressure less than an equilibrium vapor pressure of the gaseous substance, the data relating to the film thickness as a function of said pressure); computing Young's modulus of said film from said data; and outputting said computed Young's modulus of said film.

In an alternate embodiment, the program storage device may be readable by a machine and encoding a program of instructions for executing a method. The method may comprise the steps of: loading data (the data obtained by performing at least one elipsometric measurement on a film, formed on a substrate, the substrate being located in a pressurizable chamber filled with a gaseous substance at a pressure being less than an equilibrium vapor pressure of said gaseous substance, the data relating to the film thickness and refractive index); determining whether pore-killers are present in said film based on said data; and displaying a result of said determining step.

It should be understood that the programs, processes, methods and apparatus described herein are not related or limited to any particular type of computer or network apparatus (hardware or software), unless indicated otherwise. Various types of general purpose or specialized computer apparatus or computing device may be used with or perform operations in accordance with the teachings described herein.

It should further be understood that a hardware embodiment may take a variety of different forms. The hardware may be implemented as an integrated circuit with custom gate arrays or an application specific integrated circuit ("ASIC"). The embodiment may also be implemented with discrete hardware components and circuitry. In particular, it is understood that the logic structures and method steps described in the flow diagrams may be implemented in dedicated hardware such as an ASIC, or as program instructions carried out by a microprocessor or other computing device.

The claims should not be read as limited to the described order of elements unless stated to that effect. In addition, use of the term "means" in any claim is intended to invoke 35 U.S.C. §112, paragraph 6, and any claim without the word "means" is not so intended. Therefore, all embodiments that come within the scope and spirit of the following claims and equivalents thereto are claimed as the invention.

What is claimed is:

1. A method for determining Young's modulus of a film, formed on a substrate, said substrate being located in a pressurizable chamber filled with a gaseous substance, said method comprising the steps of:
    performing at least one ellipsometric measurement on said film at a pressure less than an equilibrium vapor pressure of said gaseous substance to determine data on the film thickness as a function of said pressure; and
    determining said Young's modulus of said film from said data.

2. A method as claimed in claim 1, further comprising the step of:
    accepting or rejecting the film based on comparison of said Young's modulus with a predetermined value,
    wherein said step of accepting or rejecting performs quality testing of the film.

3. A method as claimed in claim 1,
    wherein said film is produced based on parameters for a film production process, and
    further comprising the step of changing the parameters of said film production process based on comparison of said Young's modulus with a predetermined value,
    wherein said step of changing the parameters performs on-line process control of the film production process.

4. A program storage device readable by a machine and encoding a program of instructions for executing a method comprising the steps of:
    loading data, said data obtained by performing at least one ellipsometric measurement on a film formed on a substrate, said substrate being located in a pressurizable chamber filled with a gaseous substance at a pressure less than an equilibrium vapor pressure of said gaseous substance, said data relating to the film thickness as a function of said pressure;
    computing Young's modulus of said film from said data; and
    outputting said computed Young's modulus of said film.

5. A method for determining pore size distribution of a film formed on a substrate using a gaseous substance, said substrate being within a pressurizable chamber at a chamber temperature, said method comprising the steps of:
    setting said chamber to a modified pressure, the modified pressure being less than equilibrium vapor pressure of said gaseous substance at the chamber temperature;
    admitting a gaseous substance in said chamber;
    performing at least one ellipsometric measurement to determine optical characteristics at said modified pressure and at said chamber temperature; and
    calculating said pore size distribution of said film.

6. A method for determining the presence of pore-killers in a film formed on a substrate, said substrate being within a pressurizable chamber at a chamber temperature filled with a gaseous substance said method comprising the steps of:

performing at least one ellipsometric measurement at a pressure being less than equilibrium vapor pressure of said gaseous substance at the chamber pressure to determine data relating to the refractive index and thickness of said film; and determining whether pore-killers are present in said film based on said data.

7. A method as claimed in claim 6, further comprising the step of:

accepting or rejecting the film based on said presence of said pore-killers, wherein the step of accepting or rejecting performs quality testing of the film.

8. A method as claimed in claim 6, wherein said film is produced based on parameters for a film production process, and further comprising the step of changing the parameters of said film production process based on said presence of said pore-killers.

wherein said step of changing the parameters performs on-line process control on the film production process.

9. A program storage device readable by a machine and encoding a program of instructions for executing a method comprising the steps of:

loading data, said data obtained by performing at least one ellipsometric measurement on a film, formed on a substrate, said substrate being located in a pressurizable chamber filled with a gaseous substance at a pressure being less than an equilibrium vapor pressure of said gaseous substance, said data relating to the film thickness and refractive index;

determining whether pore-killers are present in said film based on said data; and displaying a result of said determining step.

10. A method for determining the amount of pores of at least two different sizes of a film formed on a substrate using a gaseous substance, said substrate being within a pressurizable chamber at a chamber temperature, said method comprising the steps of:

setting said chamber to a modified pressure, the modified pressure being less than equilibrium vapor pressure of said gaseous substance at the chamber temperature;

admitting a gaseous substance in said chamber;

performing at least one ellipsometric measurement to determine optical characteristics at said modified pressure and at said chamber temperature; and calculating said amount of pores of at least two different sizes of said film.

* * * * *